(12) United States Patent
Farr

(10) Patent No.: US 9,271,637 B2
(45) Date of Patent: Mar. 1, 2016

(54) SOLID STATE ILLUMINATION FOR ENDOSCOPY

(71) Applicant: Vivid Medical Inc., Palo Alto, CA (US)

(72) Inventor: Mina Farr, Palo Alto, CA (US)

(73) Assignee: VIVID MEDICAL INC., Palo Alto, CA (US)

( * ) Notice: Subject to any disclaimer, the term of this patent is extended or adjusted under 35 U.S.C. 154(b) by 0 days.

(21) Appl. No.: 13/936,912

(22) Filed: Jul. 8, 2013

(65) Prior Publication Data

US 2013/0296652 A1 Nov. 7, 2013

Related U.S. Application Data

(63) Continuation of application No. 11/233,684, filed on Sep. 23, 2005, now Pat. No. 8,480,566.

(60) Provisional application No. 60/612,889, filed on Sep. 24, 2004.

(51) Int. Cl.
*A61B 1/06* (2006.01)
*A61B 1/00* (2006.01)
(Continued)

(52) U.S. Cl.
CPC ............ *A61B 1/0676* (2013.01); *A61B 1/0051* (2013.01); *A61B 1/00096* (2013.01); *A61B 1/00179* (2013.01); *A61B 1/04* (2013.01);
(Continued)

(58) Field of Classification Search
CPC .. A61B 1/0008; A61B 1/0623; A61B 1/0676; A61B 1/0684; A61B 1/06
USPC ............... 600/179, 178, 160, 129, 166, 111; 362/574; 348/68, 45
See application file for complete search history.

(56) References Cited

U.S. PATENT DOCUMENTS 4,602,281 A * 7/1986 Nagasaki et al. ............... 348/69
4,884,133 A * 11/1989 Kanno et al. .................... 348/68
(Continued)

FOREIGN PATENT DOCUMENTS

JP   05-285154 A   11/1993
JP   05-337073     12/1993
(Continued)

OTHER PUBLICATIONS

Backman, V.; Gurfar, R.; Badizadegan, K.; Itzkan, I.; Dasari, R.R.; Perelman, L.T.; Feld, M.S. "Polarized light scattering spectroscopy for quantitative measurement of epithelial cellular structures in situ," IEEE Journal of Selected Topics in Quantum Electronics, vol. 5, No. 4, pp. 1019-1026, Jul./Aug. 1999.

(Continued)

*Primary Examiner* — John P Leubecker
(74) *Attorney, Agent, or Firm* — Maschoff Brennan

(57) ABSTRACT

A device for illuminating a body cavity may include an elongate tube, at least one lens element, and at least one deployable element. The elongate tube may include an internal lumen extending between a distal opening at a distal end and a proximal opening at a proximal end opposite the distal end. The at least one lens element may extend substantially across a diameter of the internal lumen of the elongate tube. The at least one deployable element may include a light source. The at least one deployable element may be operably coupled to a region of the elongate tube proximate the distal end and may be configured to be moved between an insertion position and a deployed position.

13 Claims, 19 Drawing Sheets

(51) Int. Cl.
*A61B 1/005* (2006.01)
*A61B 1/04* (2006.01)
*A61B 1/07* (2006.01)
*A61B 1/12* (2006.01)
*A61B 19/00* (2006.01)

(52) U.S. Cl.
CPC ............. *A61B1/042* (2013.01); *A61B 1/063* (2013.01); *A61B 1/0607* (2013.01); *A61B 1/0615* (2013.01); *A61B 1/0623* (2013.01); *A61B 1/0653* (2013.01); *A61B 1/0684* (2013.01); *A61B 1/07* (2013.01); *A61B 1/126* (2013.01); *A61B 2019/521* (2013.01); *A61B 2019/5206* (2013.01)

(56) References Cited

U.S. PATENT DOCUMENTS

| | | | |
|---|---|---|---|
| 5,025,778 A | 6/1991 | Silverstein et al. | |
| 5,166,787 A * | 11/1992 | Irion | 348/75 |
| 5,305,121 A | 4/1994 | Moll | |
| 5,381,784 A | 1/1995 | Adair | |
| 5,494,483 A | 2/1996 | Adair | |
| 5,538,497 A | 7/1996 | Hori | |
| 5,647,840 A | 7/1997 | D'Amelio | |
| 5,810,715 A * | 9/1998 | Moriyama | 600/144 |
| 5,895,350 A | 4/1999 | Hori | |
| 5,908,294 A * | 6/1999 | Schick et al. | 433/29 |
| 6,007,484 A * | 12/1999 | Thompson | 600/173 |
| 6,066,090 A * | 5/2000 | Yoon | 600/113 |
| 6,277,064 B1 | 8/2001 | Yoon | |
| 6,648,816 B2 | 11/2003 | Irion et al. | |
| 6,916,286 B2 | 7/2005 | Kazakevich | |
| 6,986,738 B2 * | 1/2006 | Glukhovsky et al. | 600/109 |
| 7,029,435 B2 | 4/2006 | Nakao | |
| 7,559,892 B2 * | 7/2009 | Adler et al. | 600/180 |
| 2002/0001202 A1 | 1/2002 | Williams et al. | |
| 2002/0007110 A1 * | 1/2002 | Irion | 600/170 |
| 2002/0049367 A1 * | 4/2002 | Irion et al. | 600/173 |
| 2002/0099267 A1 | 7/2002 | Wendlandt et al. | |
| 2002/0143239 A1 * | 10/2002 | Henzler | 600/179 |
| 2002/0161283 A1 | 10/2002 | Sendai | |
| 2002/0193664 A1 * | 12/2002 | Ross et al. | 600/178 |
| 2003/0050534 A1 * | 3/2003 | Kazakevich | 600/178 |
| 2003/0120130 A1 | 6/2003 | Glukhovsky et al. | |
| 2004/0077930 A1 * | 4/2004 | Guenier et al. | 600/170 |
| 2004/0147806 A1 | 7/2004 | Adler | |
| 2004/0267095 A1 * | 12/2004 | Miyake et al. | 600/175 |
| 2005/0038317 A1 * | 2/2005 | Ratnakar | 600/101 |
| 2005/0038321 A1 | 2/2005 | Fujita et al. | |
| 2005/0059860 A1 | 3/2005 | Matsumoto et al. | |
| 2005/0096502 A1 | 5/2005 | Khalili | |
| 2005/0154262 A1 | 7/2005 | Banik et al. | |
| 2005/0165272 A1 * | 7/2005 | Okada et al. | 600/114 |
| 2005/0182297 A1 | 8/2005 | Gravenstein et al. | |
| 2005/0197536 A1 * | 9/2005 | Banik et al. | 600/179 |
| 2005/0234296 A1 * | 10/2005 | Saadat et al. | 600/129 |
| 2005/0288555 A1 * | 12/2005 | Binmoeller | 600/160 |
| 2006/0041193 A1 | 2/2006 | Wright et al. | |
| 2006/0063976 A1 * | 3/2006 | Aizenfeld et al. | 600/179 |
| 2006/0069313 A1 | 3/2006 | Couvillon, Jr. et al. | |
| 2006/0149129 A1 * | 7/2006 | Watts et al. | 600/113 |
| 2006/0184048 A1 * | 8/2006 | Saadat | 600/478 |
| 2007/0015964 A1 | 1/2007 | Eversull et al. | |
| 2007/0049794 A1 * | 3/2007 | Glassenberg et al. | 600/109 |
| 2008/0207996 A1 | 8/2008 | Tsai | |
| 2010/0198009 A1 | 8/2010 | Farr et al. | |

FOREIGN PATENT DOCUMENTS

| | | |
|---|---|---|
| JP | 11-216113 A | 8/1999 |
| JP | 2000-245689 A | 9/2000 |
| JP | 2003-093399 A | 4/2003 |

OTHER PUBLICATIONS

International Search Report dated Apr. 23, 2012 as received in application No. PCT/US2011/052039.
Written Opinion of the International Searching Authority dated Apr. 23, 2012 as received in application No. PCT/US2011/052039.
European Office Action dated Feb. 23, 2012 as received in application No. 05 802 624.6.
CA Office Action dated Mar. 20, 2015 as received in Application No. 2,579,233.

* cited by examiner

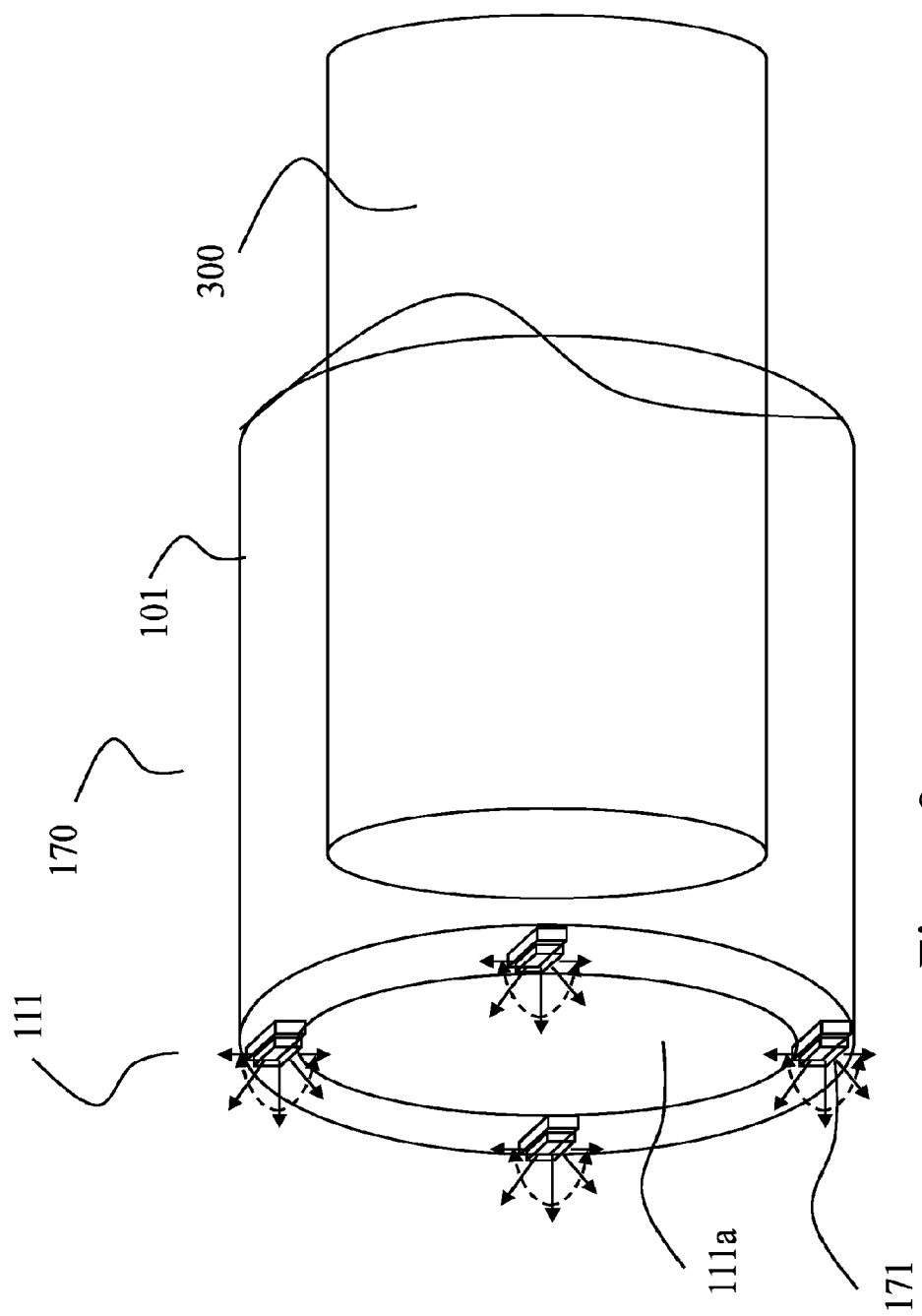

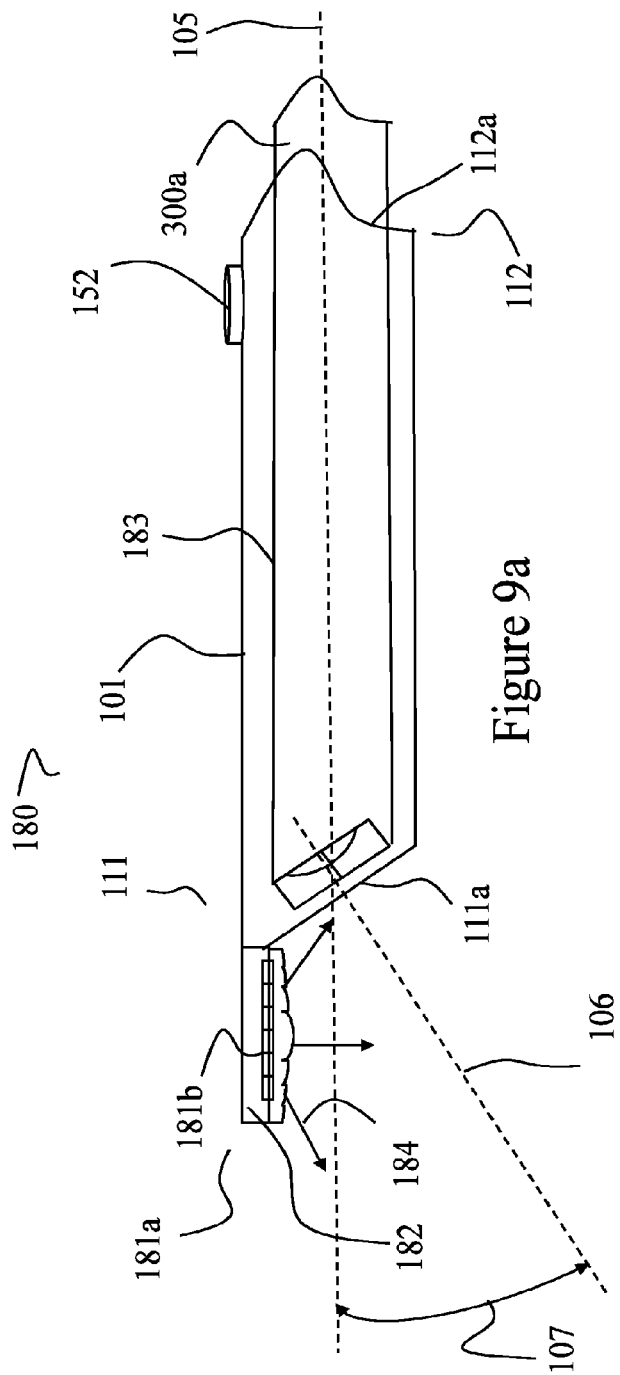
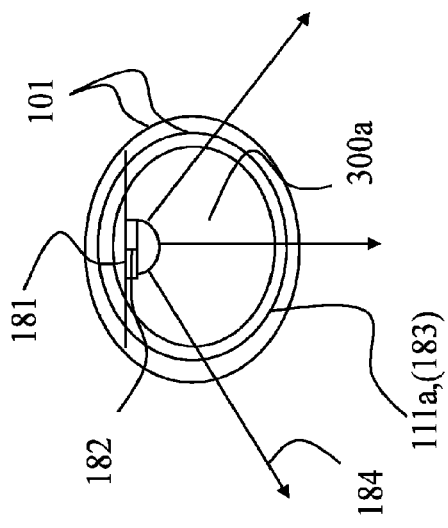
Figure 9a
Figure 9b

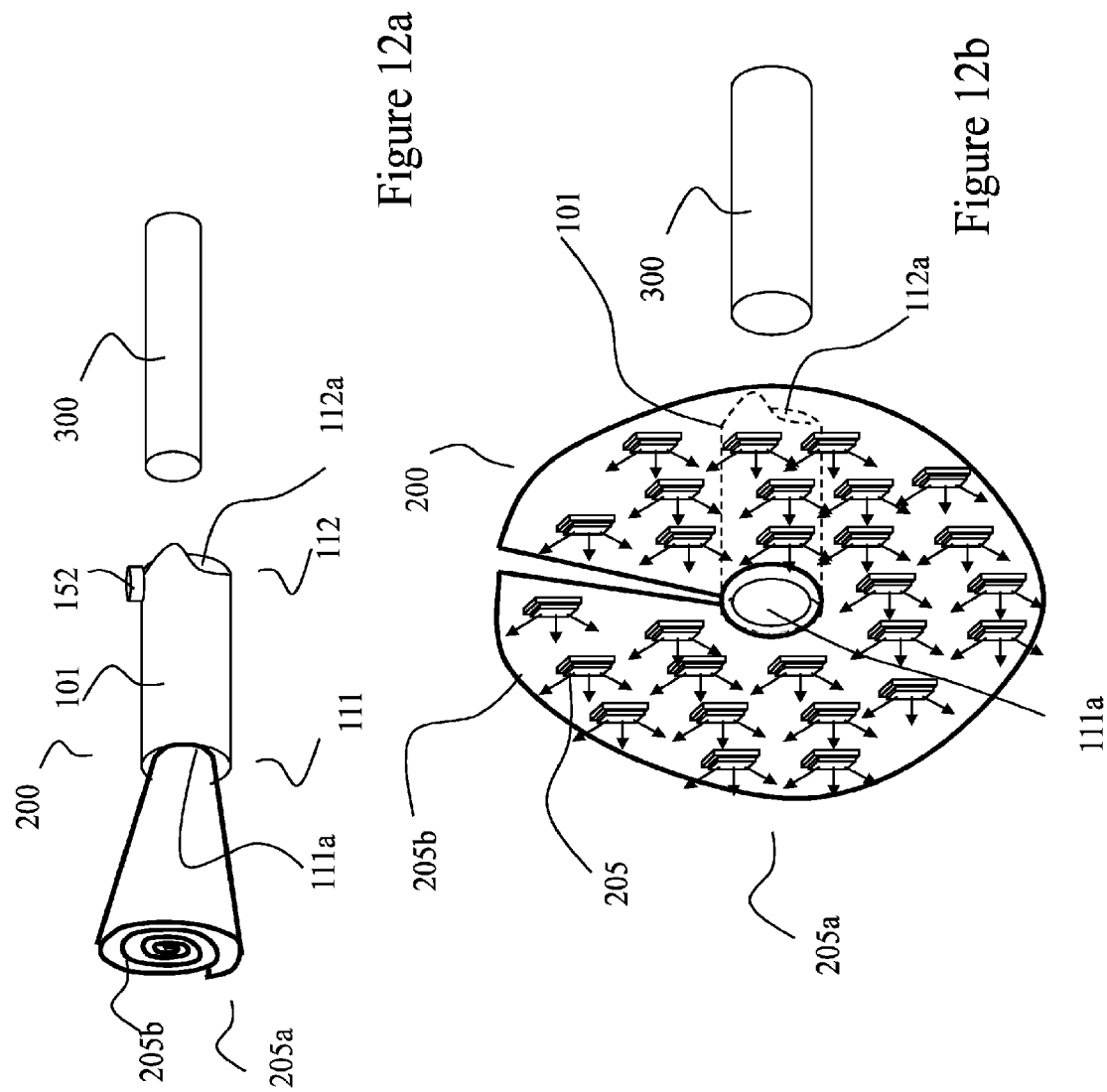

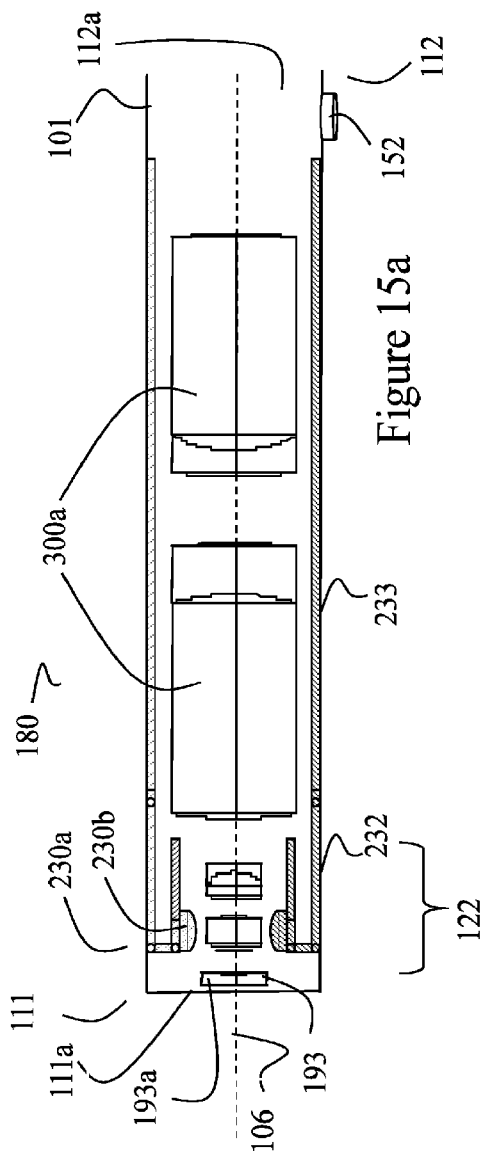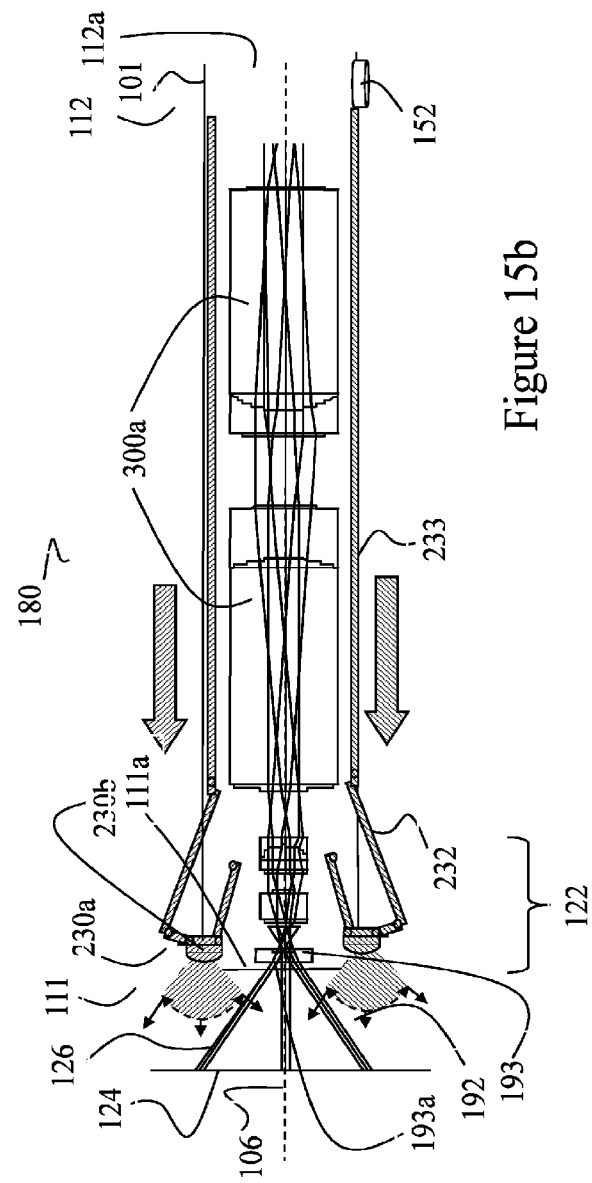

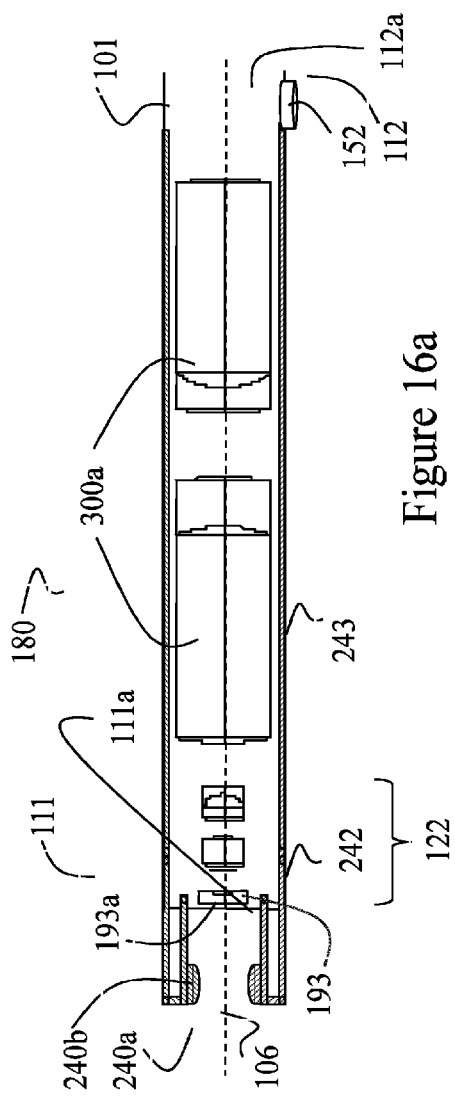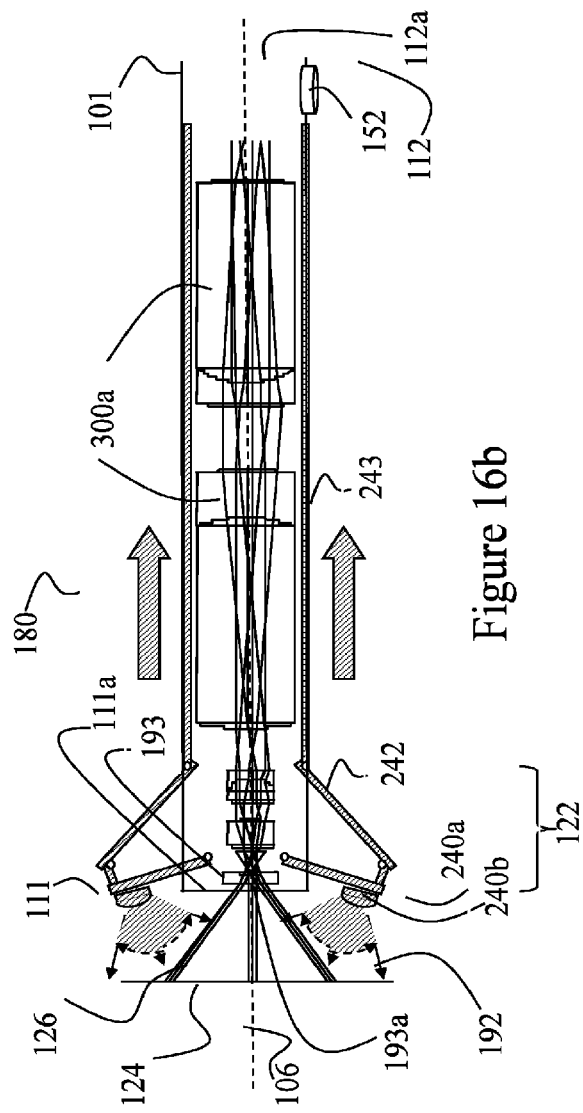
Figure 16a
Figure 16b

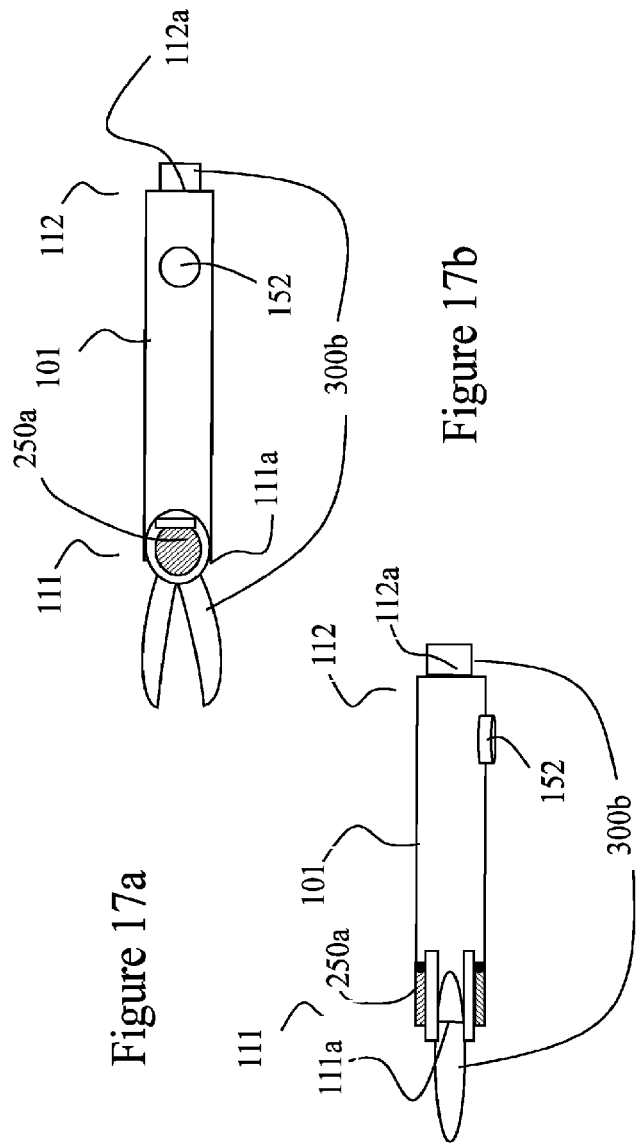
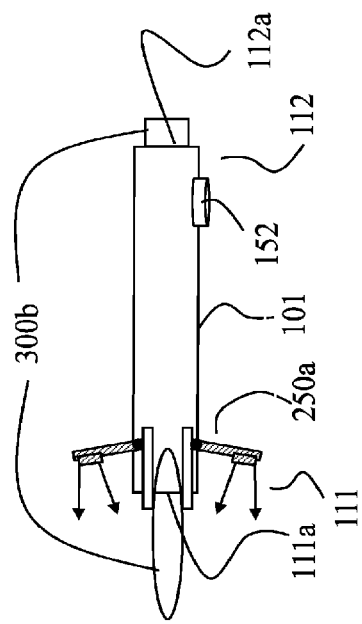
Figure 17a
Figure 17b
Figure 17c

SOLID STATE ILLUMINATION FOR ENDOSCOPY

CROSS-REFERENCE TO RELATED APPLICATIONS

This patent application is a continuation of U.S. patent application Ser. No. 11/233,684, filed Sep. 23, 2005, which claims priority to U.S. Provisional Patent Application No. 60/612,889, filed Sep. 24, 2004. The foregoing applications are incorporated herein by reference.

TECHNICAL FIELD

The present invention relates generally to apparatus for the illumination of endoscopic and borescopic fields, in minimally invasive surgical (MIS) procedures, general or diagnostic medical or industrial procedures using endoscopes or borescopes, respectively. More particularly, embodiments of the invention relate to use of Light Emitting Photodiode and other solid state light sources in endoscopic and borescopic procedures, as a means of illumination.

BACKGROUND

Laparoscopy is used in both diagnostic and surgical procedures. Currently, MIS procedures, as opposed to open surgical procedures, are routinely done in almost all hospitals. Minimally invasive techniques minimize trauma to the patient by eliminating the need to make large incisions. This both reduces the risk of infection and reduces the patient's hospital stay. Laparoscopic and endoscopic procedures in MIS use different types of endoscopes as imaging means, giving the surgeon an inside-the-body view of the surgical site. Specialized endoscopes are named depending on where they are intended to look. Examples include: cystoscope (bladder), nephroscope (kidney), bronchoscope (bronchi), laryngoscope (larynx+the voice box), otoscope (ear), arthroscope (joint), laparoscope (abdomen), gastrointestinal endoscopes, and specialized stereo endoscopes used as laparoscopes or for endoscopic cardiac surgery.

The endoscope may be inserted through a tiny surgical incision to view joints or organs in the chest or abdominal cavity. More often, the endoscope is inserted into a natural body orifice such as the nose, mouth, anus, bladder or vagina. There are three basic types of endoscopes: rigid, semi-rigid, and flexible. The rigid endoscope comes in a variety of diameters and lengths depending on the requirements of the procedure. Typical endoscopic procedures require a large amount of equipment. The main equipment used in conjunction to the visual part of the endoscopic surgery are the endoscope body, fiber optics illumination bundles, illumination light source, light source controller, imaging camera, camera control module, and video display unit.

The laparoscope is a rigid endoscope as illustrated in FIG. 1. It allows for visualization of the abdominopelvic cavities for diagnostic or surgical techniques. The laparoscope is inserted into the peritoneal cavity via a cannula that runs through the abdominal wall. There are many different features of laparoscopes, such as the size and field of vision, which determine the effectiveness of the instrument.

As illustrated in FIG. 1, the basic laparoscope is made up of a long thin tube 101 with an eyepiece 103 at one end for viewing into the patient. Fiber optic light introduced to the endoscope at fiber port 102, and launched into fiber optics 123 (FIG. 3) and 138 (FIG. 4), passes through the endoscope body 101, illuminating the area 124 that is being observed, as illustrated by radiation pattern 125 in FIG. 3. Laparoscopes are characterized by diameter and the direction of view. The direction of view is the angle 107 between the axis of the laparoscope 105 and the center field of view 106, as illustrated in FIG. 1. Typical endoscopes have lengths of approximately 30 cm and diameters in the range of 4 to 10 mm. Laparoscopes consist of two important lenses, the ocular lens at the eyepiece and the objective lens 122 at the distal end of the endoscope body 101 in FIG. 3. Other lens sets acting as relay lenses 121 in FIG. 3, are used in-between the objective lens and the eye piece or the CCD camera or image position 127. Imaging rays 126 traverse the length of the scope through all the imaging optics.

The rigid endoscope also comes in different viewing angles: 120 degree or retrograde, for viewing backward; 90 degree and 70 degree for lateral viewing; 30 degree (104 as illustrated in FIG. 1) and 45 degree for forward oblique views; and 0 degree for forward viewing. The angle of the objective lens 122 used is determined by the position of the structure to be viewed.

Other surgical instruments and tools are also inserted into the body, for the operation and specific surgical manipulation by the surgeon. The insertion is done through open tubes provided inside the endoscope body for instrument insertion, such as in gastrointestinal endoscopes, or through separate incisions in the abdominal or chest wall 113, using cannula 110 (straight or curved stainless steel or plastic tubes 101 which are inserted into a small opening or incision in the skin as illustrated in FIG. 2). The cannula opening 112a (receiving portion) at the proximal end 112 outside the body is used to receive and guide different instruments 300 inside the body, where they are exposed to the inside of the body at the distal end 111 (opening 111a) of the cannula 110 (FIG. 2). Cannulas can make a seal at the incision site 114.

In a typical gastrointestinal endoscope, a tool opening is provided at the distal end of the scope, where inserted medical instruments gain access to the body following the scope body.

Endoscopes can be diagnostic, for observation only, or operative, having channels for irrigation, suction, and the insertion of accessory instruments when a surgical procedure is planned. Thus, endoscope bodies also could provide mechanical or electrical control sections, buttons for valves such as a suction valve, a CO2 valve, a water bottle connector, a water feed, a suction port, etc. The common component that all endoscopes must be equipped with is a light guide section for illumination.

An illustration showing typical endoscope optics is shown in FIG. 3. Common imaging sections of the endoscope are an ocular or eyepiece, relay lenses 121 (in the case of rigid scopes), a flexible imaging fiber-optic bundle (in the case of flexible scopes), and an objective lens system 122. Endoscopes are either used as stand-alone units, with the surgeon looking into the scope from the ocular or eye piece of the endoscope, or in conjunction with digital cameras 127, where an image (rays 126) of the surgical site 124 is incident on the image capture device (charge coupled device or CCD) of the camera (127). Using a display device, the surgeon performs the operation looking at the image on the video monitor.

With recent technology improvements in the field of electronic imaging reducing the size of the image capture device (CCD), some endoscopes used in MIS and diagnostic procedures are equipped with a high resolution distal end camera system, commonly referred to as Chip on a Stick, one example of which is illustrated in FIG. 4. These flexible endoscopes use a CCD chip 137 at the distal end of the endoscope directly capturing the image through the objective lens 133, in which case the flexible part (132) of the endoscope body, contains only power (137a) and communication wires 137b for the CCD camera at the distal tip, rather than imaging optics 133 which is located in the rigid portion 131 of the endoscope. Light guides 138 are still necessary for this type of electronic scope to provide adequate lighting (134) of the surgical site 136 for imaging purposes.

Other, more complicated MIS systems make use of robotic surgical tools and instruments, and/or provide stereoscopic images of the surgical site for the surgeon, improving the surgeon's dexterity, precision and speed of operation. In these more sophisticated MIS imaging applications more specific types of illumination systems or multiple illuminators are used.

Endoscopes can have a variety of forms, ranging in diameter, tube length, and angle of view. However, all types of endoscopes commonly use optical fibers (123, and 138 in FIGS. 3 and 4) to illuminate the surgical site. Illumination is a very important part of laparoscopy because there is no light source inside the body. Fiber optic cold light is used to project light down the laparoscope from an external source. Large lamps with broadband output are used to couple light into the illumination light guides (123 and 138 in FIGS. 3 and 4), where light guides transfer the illumination light from the light source to the illumination fiber bundle (123, 138) inside the endoscope body 101. A typical scope attached to an illumination light guide (port 102) is shown in FIGS. 1, 3 and 4. One (FIG. 1) or more light guide bundles (FIGS. 3 and 4) are used to couple light into the endoscope illumination fiber bundles 123 and 138 of FIGS. 3 and 4.

The use of fiber bundles 123 and 138 inside the endoscope body 101 in FIG. 3 and FIG. 4, or tube 101 occupies substantial space that otherwise could have been used by the imaging optics. This can be seen in FIGS. 3 and 4, showing the fiber optic illuminators 123 and 138 sharing the endoscope body 101 with the imaging optics (121, 122, 133). Limitations on the optical lens terrain (121, 122, 133) diameter, as well as the imaging fiber bundle thickness, correlate directly to the imaging resolution vs. size of the image. The larger the lens diameter or imaging bundle thickness, the better the resolution of the endoscope for a certain field of view (FOV) or image size. This is the main reason that larger diameter scopes are considered better in optical quality than narrower scopes. However, large scope diameters are not desirable for certain operations where space is limited on the operation site.

Different illumination fiber geometries are used to reduce the space constraint inside the scope body. For this reason, and to have a more uniform illumination, the imaging fiber bundles are also split in some cases to have two or more points of illumination at the distal end of the scope. In other types of scopes, illumination is made into a circular ring pattern at least at the distal end of the endoscope, similar to the ring illumination of microscopy.

The light source for the endoscope is either a xenon bulb, which creates a high intensity white light suitable for smaller-diameter endoscopes, a halogen bulb, which creates a yellowish light suitable for general endoscopic work, or a Metal Halide lamp. Since most broadband light sources also produce large amounts of Infrared Red (IR) wavelength light, IR cut filters and lamp dichroic reflectors (heat blocking filters and reflectors that reduce the radiation usually associated with heat production) are used in the illumination light source to prevent the transfer of IR radiation to the body. Thus, broadband visible cold light is highly desirable in laparoscopic procedures providing decreased thermal injury to tissues. Since most CCD cameras are also sensitive to IR radiation (due to Silicon absorption spectrum), extra IR cut filters are used in front of the camera to prevent glare caused by IR radiation in the camera.

Despite the precautions used in reducing the IR radiation, in actuality some amount of infrared radiation in addition to the visible light enters the fiber optic cable, and is transmitted through the cable and scopes (port 102, fibers 123 and 138) into the body. When the light leaves the endoscope tip, the level of infrared radiation has usually been reduced to a safe level through absorption by the optical fibers in the endoscope, and substantial losses at the cable connections (port 102). However, if the cable is not connected to the endoscope, the infrared output is not reduced sufficiently and even could have the capability of igniting some materials if the cable is left at close proximity to absorbing combustible material. This hazard exists in fiber illumination cables with high intensity light sources.

Additionally, higher outputs not only increase the risk of fire, but may introduce the risk of burns during close-range inspection of tissue with the endoscopes. Absorption of high-intensity radiation at visible light wavelengths may also cause tissue heating, where additional filtering of infrared wavelengths may not eliminate this hazard. Furthermore, with the increasing use of television systems with video cameras connected to the endoscopes, many physicians operate light sources at their maximum intensities and believe they need even greater light intensities to compensate for inadequate illumination at peripheral areas of the image where the illumination intensity falls rather rapidly using today's standard illumination fiber guides.

Typical light sources are also deficient in their flux and color management of their spectral output. A typical lamp spectral output requires time to come to an acceptable level during the warm-up procedure, both in terms of lumens output as well as color quality or white point on the color gamut. The color temperature of the lamp based illuminators, are typically deficient in producing the desirable color temperature (daylight color temperature of 5600 Kelvin) for typical endoscopic procedure. Color content of the lamp output also typically shifts during the life time of the lamp. Thus it is usually required to perform a white color balance adjustment in the camera controller each time an endoscope is used subsequent to the light source warm-up procedure to obtain realistic color image. A repeat of the white color balance adjustment may also be necessary if the lamp intensity is adjusted through a large range.

Typical high power lamps also have very limited life time, measured in hours (Typically 50, 500, or 1000 hours for Halogen, Xenon or Metal Halide depending on the lamp), where the light output of the lamp degrades to about one half of its original light output. Typical lamp manufacturers typically do not specify or have a failure criteria based on the color quality for the lifetime of the lamp.

Complicated and bulky optical schemes are incorporated in the light guide optical sources for effective coupling of the light into the illumination fiber bundles (123 and 138). Special non-imaging optics such as glass rods, and lens elements are used to also uniformly couple light into all the fibers inside the illumination fiber bundle. All these increase the cost and also size of having high brightness, uniform fiber optic illumination light sources. Typical high brightness light sources also incorporate powerful fans to dissipate the large amount of heat generated inside the light source package. In fact in a typical endoscopic procedure, light sources are one of the main sources of heat generation and the associated fans on the light sources are one of the main sources of noise in the surgical environment. Large package size of high power lamps also add extra burden to the premium space in a diagnostic and surgical environment.

Light sources normally give off electromagnetic interference (EMI), where the starting pulses from the lamp could reset or otherwise interfere with other digital electronics devices in today's surgical environment.

In an operating environment, the light source(s) are placed at a distance, on a table top or rack, mounted away from the patient and the endoscope. Fiber optic light bundles to transfer the light from the light source to the endoscope are used as light links between the light source and the endoscope. These fiber bundles are not only bulky and expensive, but their price increases by the length of the fiber bundle, whereas the amount of light transmitted goes down as the length of the fiber bundle increases. To conveniently place the light source and fiber bundle away from the operational site, longer fiber bundles are necessary, however the attenuation, or drop in the transmitted optical flux increases with the length of the fiber used as well, requiring more powerful light sources.

Use of fiber optic light guides as a means of transfer of illumination light from the proximal 122 to the distal end 111 of the endoscope also increases the chance of relative light loss. The relative optical light-loss measurement quantifies the degree of light loss from the light source to the distal tip of the endoscope. The relative light loss will increase with fiber-optic (123, 138) damage. Extra heat will also be generated in the broken fiber ends inside the endoscope. In fact the major failure mode for the fiber optic bundles delivering the light to the endoscope, and the optical system inside the endoscope is breakage of the fibers.

As illustrated in FIGS. 1, 3 and 4, the illumination fiber bundle(s) port 102 commonly join the endoscope body at some angle near the ocular (103) at the proximal side 112 of the endoscope. The fiber guide body and the main endoscope body 101 are commonly joined together in a welding process at joint 108 illustrated in FIG. 1. The construction and design of this welded joint is often a weakness in the endoscope manufacturing and use, where after many operations, high temperature and high humidity sterilizations, and successive handling, this welded joint could get damaged and break, exposing the internal parts of the scope to the environment when the seal is broken.

Color CCD cameras use alternate color dies on the individual CCD pixels, to capture color images. Green and red, and green and blue pixels are alternated in rows. This spatial color sampling limits the color resolution of the color CCD cameras, since each pixel is dedicated to capturing a single color in the color image.

Three (3) chip CCD cameras (red CCD chip, blue CCD chip, and green CCD chip) are also used in high resolution applications, where all the pixels in each CCD are dedicated to detecting the single color content of the image. The individual color captured images from the 3 CCDs are then put together electronically, as the multi-color image is reproduced on the viewing display. Three chip CCD cameras are expensive and bulky.

BRIEF DESCRIPTION OF THE DRAWINGS

To further clarify the above and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 8 illustrates a cannula with built in LED illuminators at the distal end of the cannula;

FIGS. 9a and 9b illustrate an angled endoscope with modified distal tip, incorporating an array of LEDs for illumination of the surgical site;

FIGS. 12a and 12b illustrate insertion and deployment of a flexible membrane with built in LED illuminators, to light the surgical area inside the body;

FIGS. 15a and 15b illustrate possible deployment of LED illuminators stored next to the objective lens of a rigid body endoscope;

FIGS. 16a and 16b illustrate possible deployment of LED illuminators stored along the distal tip of a rigid body endoscope;

FIGS. 17a, 17b, and 17c illustrate LED illuminators built into the body of a surgical instrument or tool, with possible deployment during operation to illuminate the surgical site.

DETAILED DESCRIPTION

Figure 1:
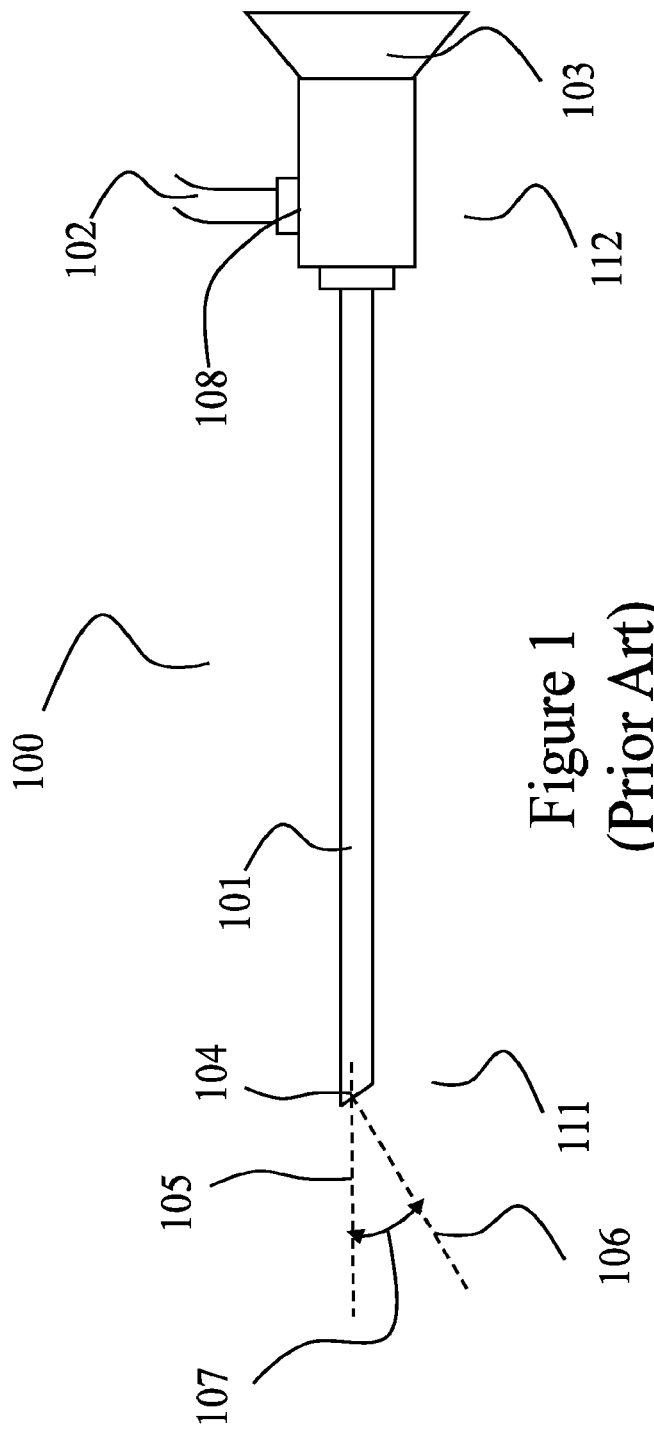
FIG. 1 illustrates a typical angled endoscope, with fiber optic light port for illumination, and an eye piece for viewing.
Figure 2:
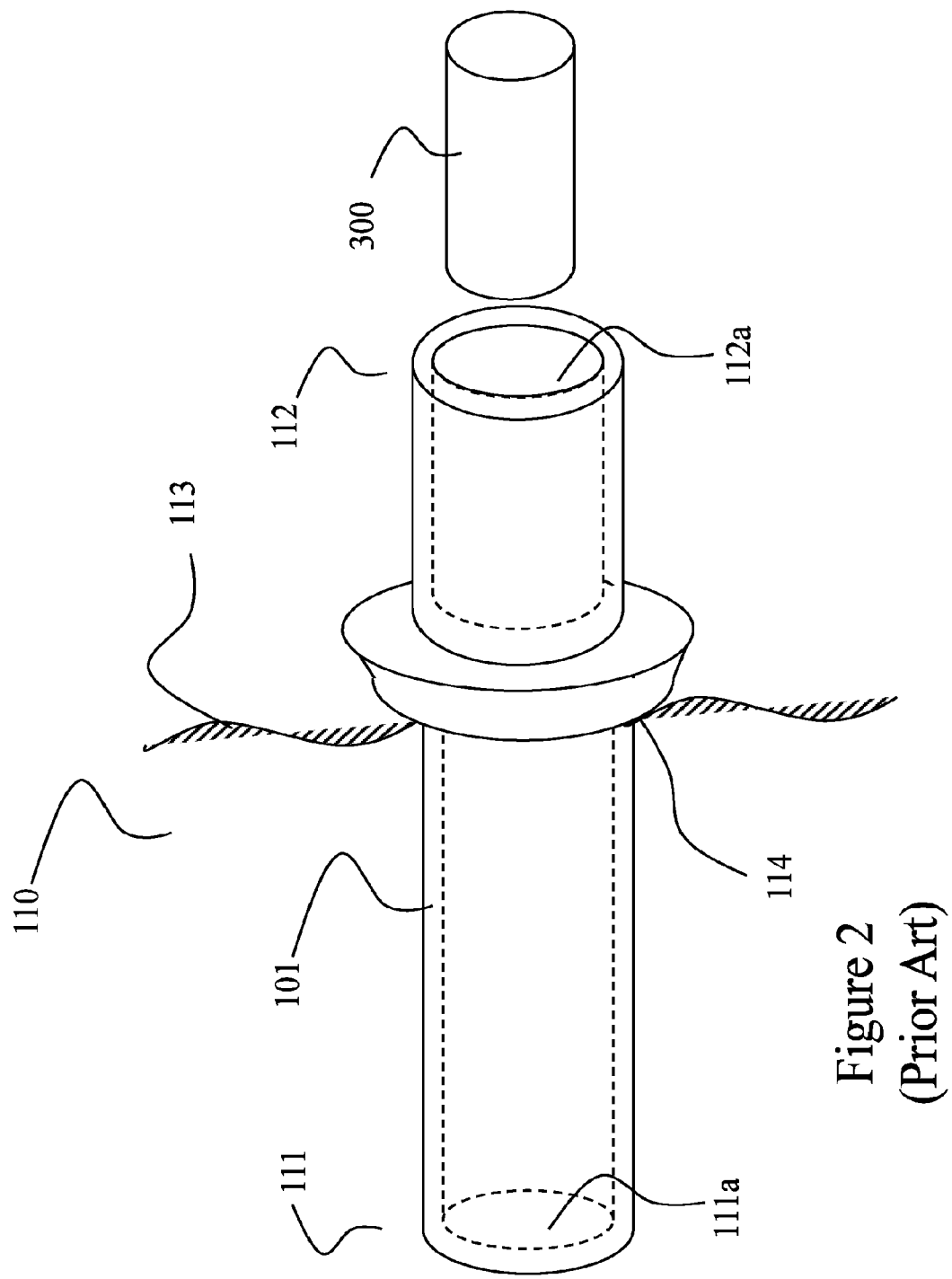
FIG. 2 illustrates a cannula inserted into the body cavity, providing means to insert an instrument into the body.

Exemplary embodiments of the invention concern monochromatic or polychromatic solid state light sources such as high power Light Emitting Devices (LEDs) and Laser Diodes as a means of illumination in a diagnostic or surgical endoscopic procedures, or functional borescopic systems. In particular, these solid state light sources are incorporated at the distal end of the endoscope, borescope, surgical or industrial tools, and the tip end of cannulas and other functional devices. They can also be incorporated in an illumination body that is inserted separately, or in conjunction with a lighted or dark scope, into the body. The illumination of an object inside a body, a body herein being defined as at least a portion of a human, animal or physical object not easily accessible, is performed to detect the modified light, image the object, or manipulate a change in the object. The solid state illumination schemes of the present invention can replace, or can be used in addition to, the conventional fiber optic illumination system and other diagnostic devices such as ultrasound imaging used in endoscopy and borescopy.

Use of such solid state sources inside a cavity in the body, replaces variety of instruments otherwise needed for the same purpose, such as an external light source, fiber light guides, and means of transmitting the light to the desired object.

Exemplarily, the use of LED sources has several advantages over the conventional external white light source. With an LED based illumination, a true, visible light source with no IR content is available for the endoscopic application. Therefore, the complicated IR management of the light source is eliminated. There is no longer a fire hazard associated with light guides that may be left on, and no heat management inside the scope is needed.

LEDs can provide light at any region of the visible spectrum. Red, Green, and Blue LEDs (chips) in primary colors can be used together to form a white illumination, Phosphor-converted LEDs can provide white output directly without any color mixing, Infra Red (IR) or Ultraviolet (UV) LEDs can be used for their special characteristic in light transmission in the medium of insertion or the effect they have on the object of interest (151, 161, 171, 181*b*, 191, 201*b*, 203, 205, 210*b*, 220*b*, 230*b*, 240*b*, 250*a* in FIGS. 6*a* through 17*c*).

LED lifetimes are more than order of magnitude longer than bulb type light sources (50 k hours depending on the drive condition). The long life time in conjunction with the reliability associated with solid state lighting practically illuminates any lamp outages in an MIS procedure, where dependable illumination is one of the most critical parts of the system. In fact LED life time is more in line with the usage life time of most MIS surgical tools.

LED power consumption is also much lower than high power light sources. The LED illumination system is most efficient since there is no need for i) transferring light from the source through fiber optic light guides, ii) coupling the light into the scope light guides, or iii) transmitting through the fiber optic light guides through bends in the fiber. Light powers in the order of 1000 lumens are in fact possible with use of few high power LEDs.

Figure 3:
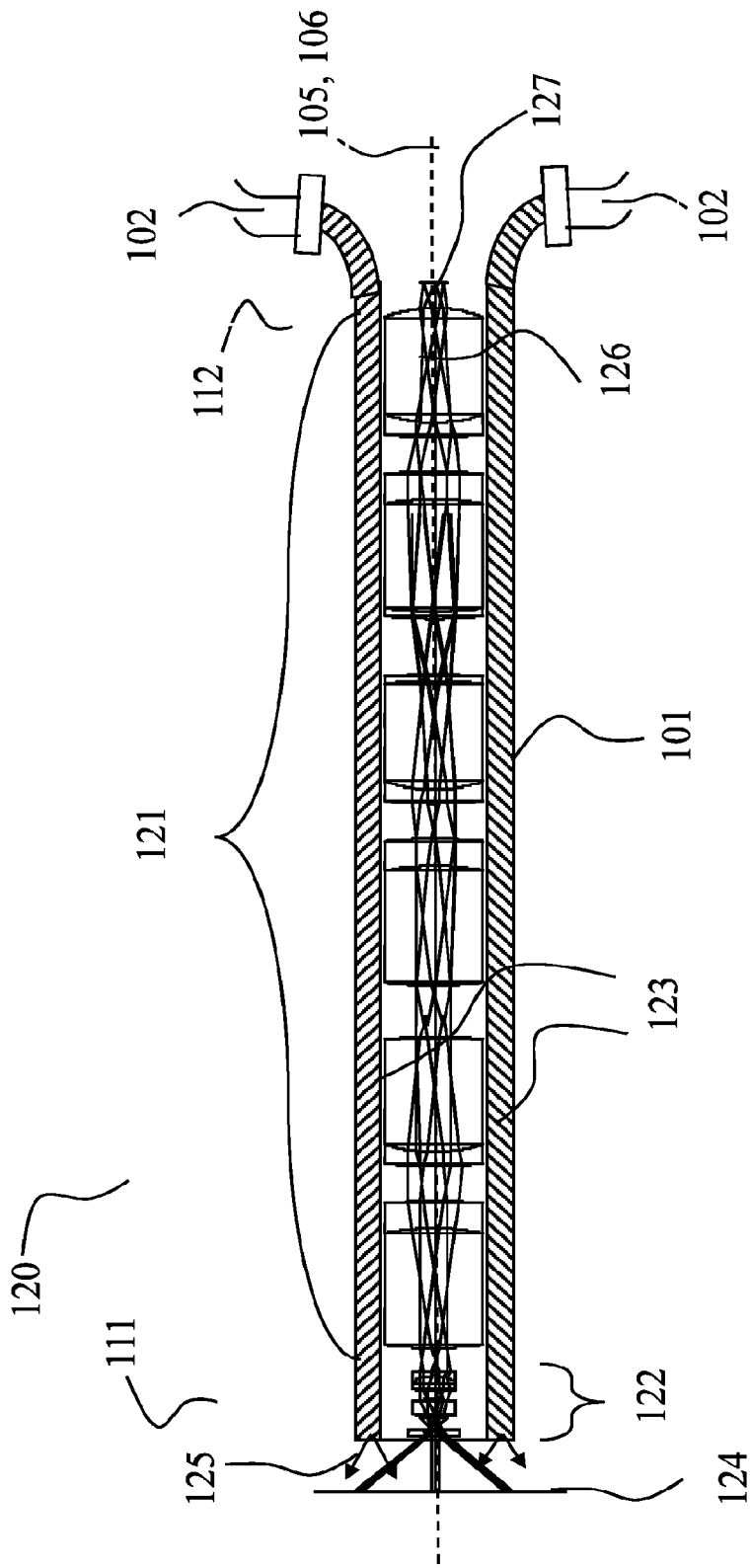
FIG. 3 illustrates the cross section of a typical zero degree, rigid endoscope with associated terrain for relay of the image through the length of the endoscope.
Figure 4:
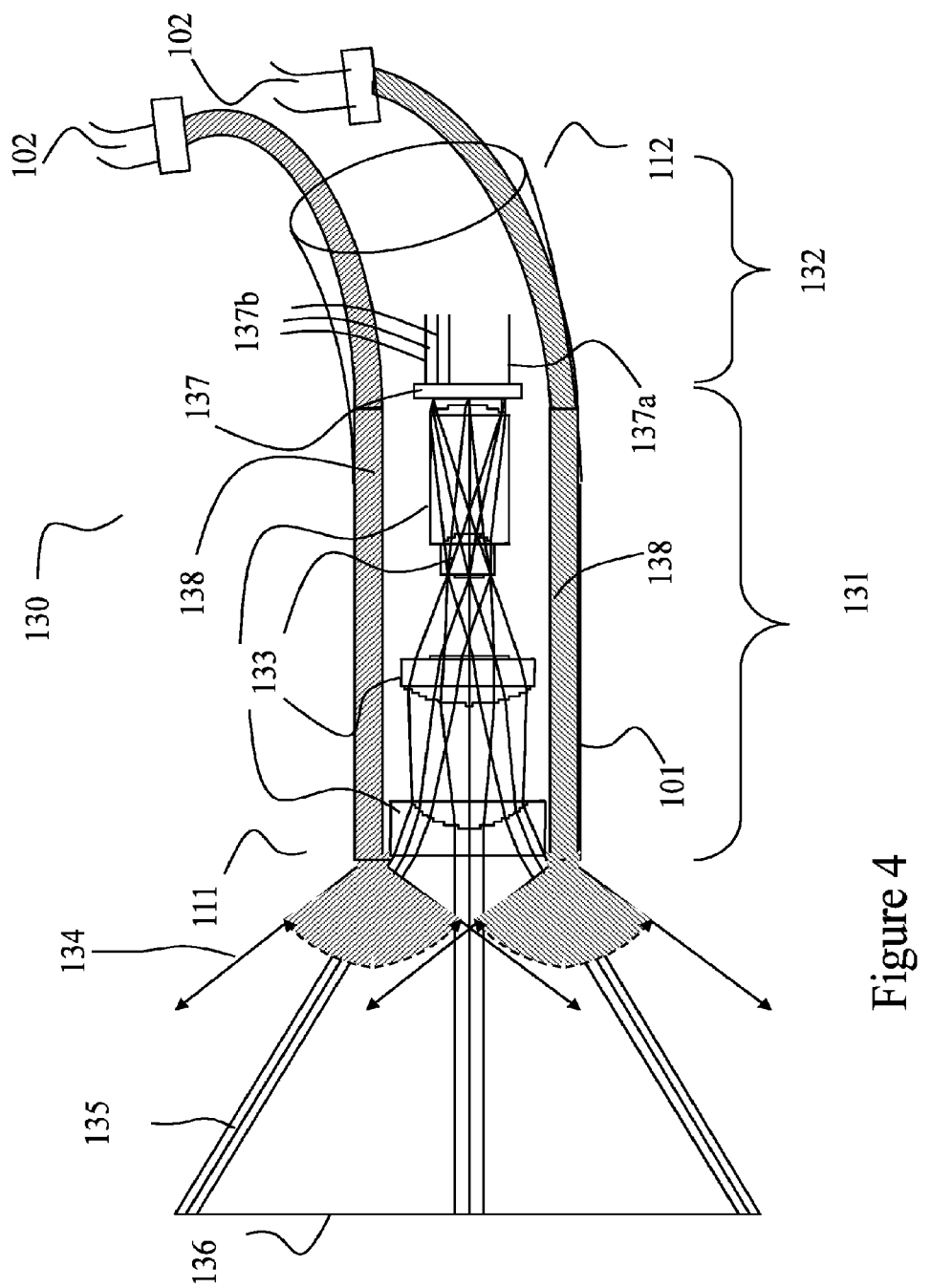
FIG. 4 illustrates the cross section of a zero degree typical flexible endoscope body (Chip on the Stick) with fiber optics illumination.

Further, LEDs are robust, and do not break, unlike fiber optic light guides (123, 138 in FIGS. 3 and 4). Properly encapsulated LEDs (chips), can withstand severe environmental conditions and cleaning procedures.

LEDs do not produce any electromagnetic interference, thus eliminating the need for complicated EMI management system such as Faraday caging. Because of size, reliability and safety of LEDs, these light sources are ideal choice for "in location" illumination of the object inside the body. Where only electrical power is transmitted to the light source inside the body along with possible electrical control signals.

By eliminating conventional fiber optic illumination guides 123 and 138 (FIGS. 3 and 4) inside the endoscope body 101, there is more space for the imaging optics (121, 122, 133) or imaging fibers, where the size directly relates to the image information transfer capability of the system. With more space available to the imaging optics (121, 122, 133), larger diameter optics and imaging fiber diameters can be used, making larger image FOVs (made by imaging rays 126 and 135) and higher resolution possible.

LEDs do not require a warm-up procedure. LEDs are capable of providing instant illumination with the exact color point at initiation. Optical power and color maintenance over the life time of the LED are also critical features of solid state light sources.

By using three color LEDs (red, green and blue chips) and synchronizing a black and white camera system to grab the three synchronized color component images (FIGS. 6*a* through 17*c*), the use of color camera chips or the high resolution 3 CCD chip cameras is eliminated. Since a single CCD camera is used to capture the three images in a time synchronized fashion, each color component image takes advantage of the full CCD image resolution by incorporating all the pixels in each color image component. Examples of exemplary embodiments of endoscopes having LED illuminators (191, 201*a*, 201*b*, 203, 210*a*, 220*a*) and CCD image cameras 137 are shown in FIGS. 4, 10, 11*a-b*, 13*a-b*, and 14*a-b*. Simple black and white CCD or CMOS camera chips (137, in FIGS. 10, 11*a-b*, 13*a-b*, 14*a-b*) are also cheaper to use, especially compared to a 3 chip CCD camera, where in effect the resolution of the synchronized black and white imaging CCD using synchronized color illumination (191, 201*a*, 203, 210*a*, 220*a*) provided by the LED chips (191, 201*b*, 203, 210*b*, 220*b*) is equivalent to a same pixel 3 CCD chip camera (FIGS. 10, 11*a-b*, 13*a-b*, 14*a-b*).

Using the color synchronized image capture device also allows the use of much higher resolution image capture devices in chip on the stick cameras (137, in FIGS. 10, 11*a-b*, 13*a-b*, 14*a-b*) where space is limited at the distal tip of the endoscope 190 for the image capture CCD. A variety of illumination configurations are possible using LED chips, where the uniformity, angle and extent of the illumination are freely controlled by the positioning and design of the LED light sources (191, 201*a*, 203, 210*a*, 220*a*).

Figure 5B:
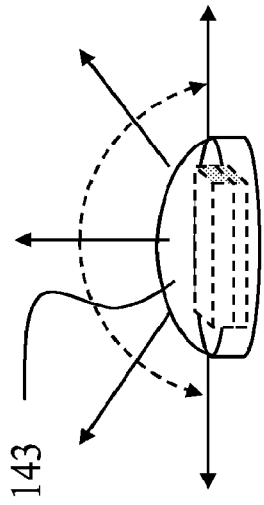
FIGS. 5a to 5d illustrate various single LED sources, without and with various encapsulation optics.
Figure 5D:
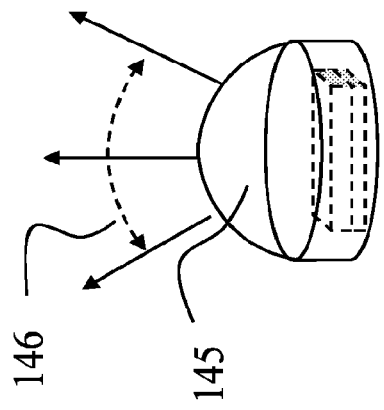
Figure 5A:
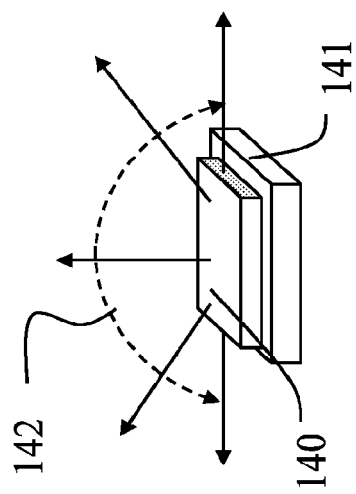

FIGS. 5*a* through 5*d* illustrate various configurations of LED output. FIG. 5*a* depicts a LED 140 disposed on a base 141. The LED 140 is unencapsulated resulting in output in the form of a Lambertian light source. This makes these solid state light sources ideal for endoscopic illumination applications where wide angular field of view needs to be properly illuminated.

A simple lensing element can also be used in the form of an LED encapsulant, where depending on the shape of the lens surface and the lens' distance from the LED surface, different angular illuminations or focusing of the light can be easily accomplished. FIG. 5*b* illustrates a simple lens encapsulation 143 maintaining the same Lambertian light output as the unencapsulated LED, however with much higher light extraction from the LED chip.

Figure 5C:
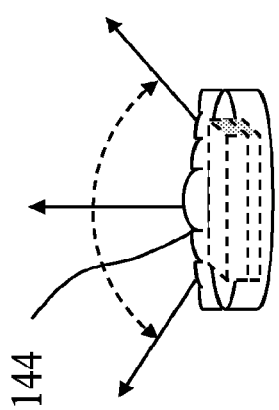

FIG. 5*c* depicts an alternate surface structure for the LED encapsulation, such as fresnel lens profile 144, diffractive optics or other refractive profiles can yield different angular extent of the encapsulated LED radiation pattern 144.

FIG. 5*d* illustrates a simple lens encapsulation where higher index encapsulation material is used in conjunction with positioning the lens surface farther away than the lens radius of curvature resulting in a substantial decrease in the angular extent of the radiation pattern 146 can be achieved.

With controllable illumination color available to 3 color chip LEDs (in 190, 201*a*, 203, 210*a*, 220*a* of FIGS. 10, 11*a-b*, 13*a-b*, 14*a-b*), the color gamut of the illumination can be changed according to the application using the drive condition for the independent color chips 190, 201*b*, 203, 210*b*, 220*b*. This is highly desirable where the information content of the surgical site 136 is mainly in a certain color, and where shifting the illumination color can increase the visibility and differentiation needed in diagnostic evaluation of the surgical scene.

Using more illumination sources (more LED chips in FIGS. 5*a*-5*d*) with other wavelengths than the three primary illumination colors, and matching the image detection (137) frame capture sequence to that of the synchronized color illumination sources (191, 201*b*, 203, 210*b*, 220*b*, in FIGS. 10, 11*a-b*, 13*a-b*, 14*a-b*), allows higher quality image capture in terms of more realistic colors. Using only primary RGB colors (RGB chips 151, 161, 171, 181b, 191, 201b, 203, 205, 210b, 220b, 230b, 240b, 250a in FIGS. 6a through 17c) the detected image color content is within the color triangle in the CIE color diagram. Adding LED chips with other colors such as amber, cyan, and magenta, increases the detected color gamut of the image substantially. With the recent color displays such as flat panel LCD displays using more than just primary color illuminators (such as with 6 LED back light illuminators), it is in fact possible to present a "true color" image to the operator that was never before possible with the 3 color CCD cameras. This can be important in certain surgical applications where the color reproduction integrity plays an important role in the surgeon's perception of the scene or diagnosis of the object.

LED illumination systems are modular, where one or multiple LED chips (151, 161, 171, 181b, 191, 201b, 203, 205, 210b, 220b, 230b, 240b, 250a in FIGS. 6a through 17c) can be inserted into the body independent of one another, via separate illumination bodies, at the distal end of an endoscope (180, 190 in FIGS. 9a-b, 10, 11a-b, 13a-b, 14a-b, 15a-b and 16a-b), or incorporated at convenient and efficient locations on surgical tool tips (FIGS. 17a-c) or cannulas (FIGS. 6a-b, 7, 8 and 12a-b).

Different solid state light sources or combination of these sources can be used to perform diagnostic as well as surgical or other functions on a body. A variety of illuminators can work in conjunction with one another and other devices to image, detect or modify the object.

Figure 6A:
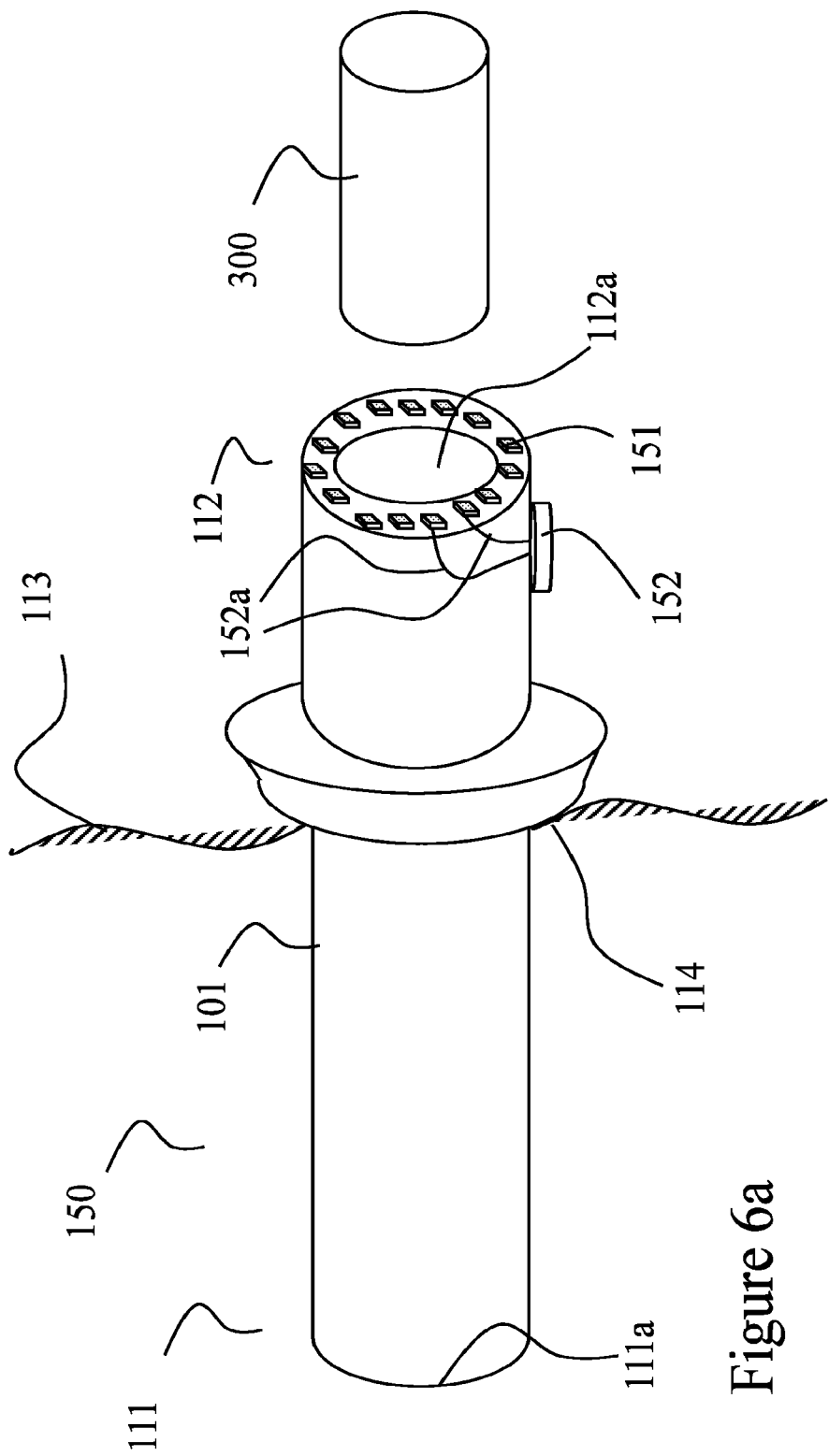
FIGS. 6a and 6b illustrate a self-lighted cannula using multiple LED sources installed at the proximal end of the cannula.
Figure 6B:
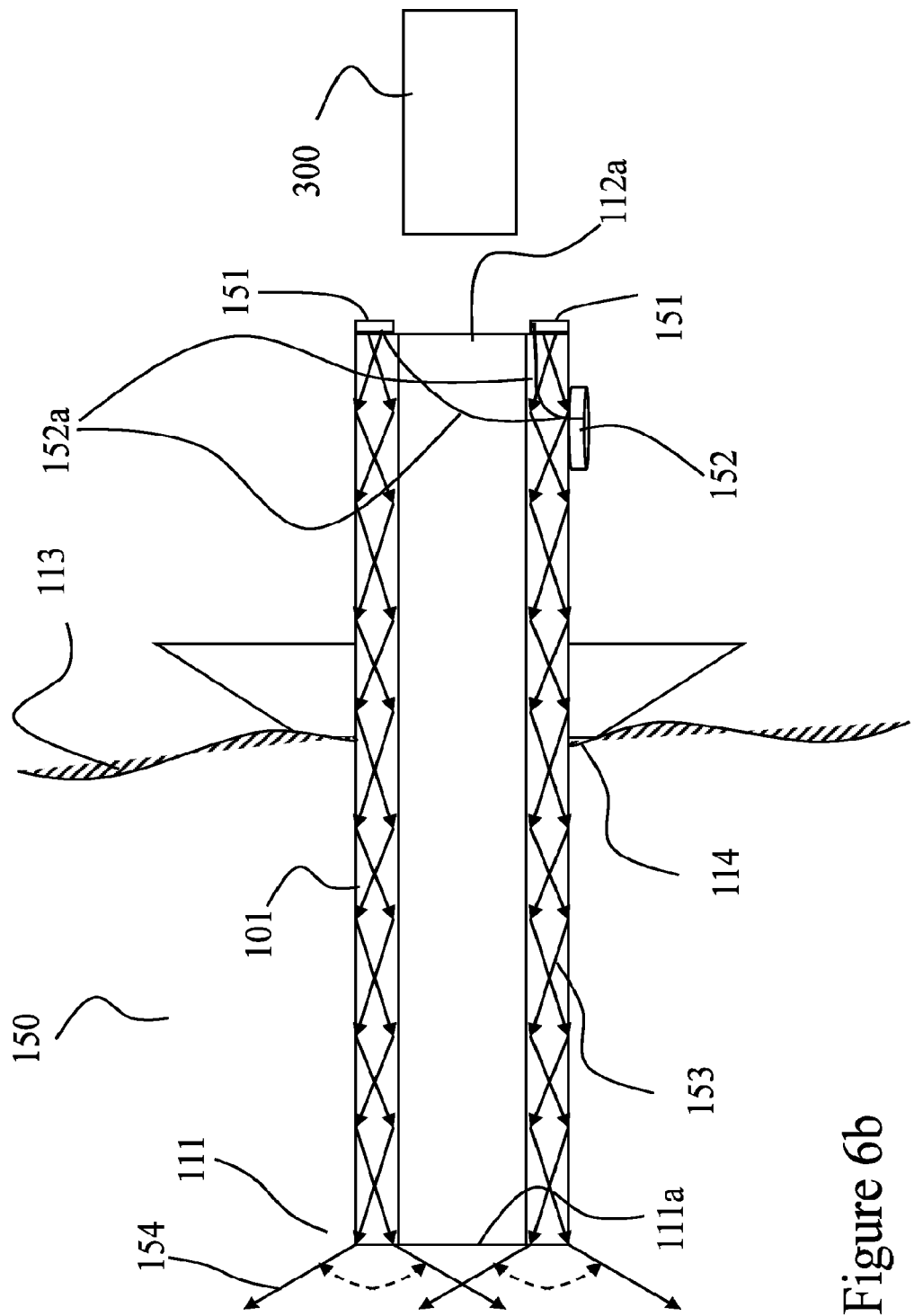

One example of an embodiment 150 of an LED illuminator according to the present invention used in a cannula body 101 is illustrated in FIGS. 6a and 6b. In this exemplary embodiment, the body 101 of the cannula 150 which is clear to the light in the visible spectrum is completely lit by white or color LED chips 151 mounted at the proximal end 112 of the cannula body 101. Electrical power to the LEDs is provided by power connection 152 (electrical lines 152a) on body 101. As illustrated in FIG. 6b, the LED light fed into the cannula body 101 goes through Total Internal Reflection as it travels the length of the cannula body 101 to the distal end 111, at which point the light leaves the cannula body 101, illuminating the surgical site and tools as indicated by radiation pattern 154.

Figure 7:
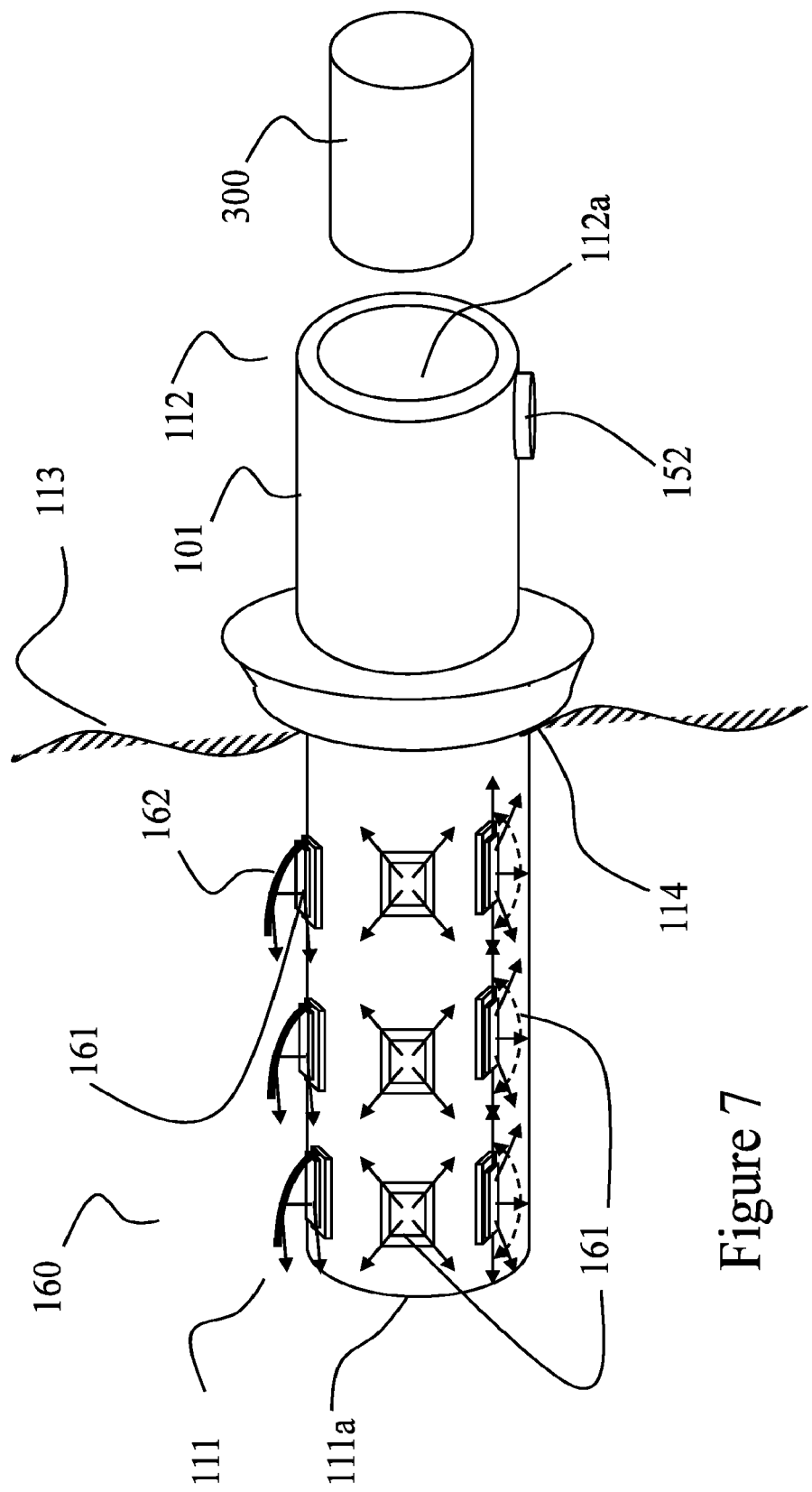
FIG. 7 illustrates a cannula body used as the illuminator for inside the body cavity.

In an alternative embodiment of a cannula 160 depicted in FIG. 7, the cannula body 101 includes near its distal end 111 surface mount white or color chips 161. A cone type reflective cover 162 for these LEDs 161 can also be inserted along with the cannula 160 into the body, where the LED light from the body 101 of the cannula is directed more towards the distal end 111 of the cannula 160.

FIG. 8 illustrates another simple embodiment of a cannula 170 with white or color LED chips 171 mounted directly at the distal end 111 of the cannula 170.

As depicted in FIGS. 9a and 9b, in an exemplary embodiment of an LED illuminated endoscope 180, an array of white or color LED (chips) 181b is built into an extension portion 181a extending from the distal tip (111) of an angled endoscope body, tube 101. The array of LED chips 181b can be encapsulated with lens elements 182 to establish the desired illumination field and uniformity 184. FIG. 9a illustrates this exemplary embodiment of endoscope 180 in the side view, and FIG. 9b is and end view illustration of such embodiment. Clear imaging port is noted as 183 on these figures (with proximal opening 112a and distal opening 111a), and the LEDs (181b) are encapsulated using a Fresnel type lens structure 182. Other tool insertion ports, multiple imaging ports for stereo imaging, or imaging ports with various Field of View (FOV), can be used in the clear area of the distal end (distal opening 111a) of the endoscope hollow tube 101. Other solid state light sources such as laser diodes or various wavelength LEDs 181b can be mounted in the vicinity of the LED sources depicted in this embodiment to perform other functions using the same device. Other forms of optics or optical elements such as lenses, polarizers and wave-plates can also be used in front of the LED illuminators 181b or detection ports (distal end opening 111a) to modify the illumination extent or for proper detection of the light.

Figure 10:
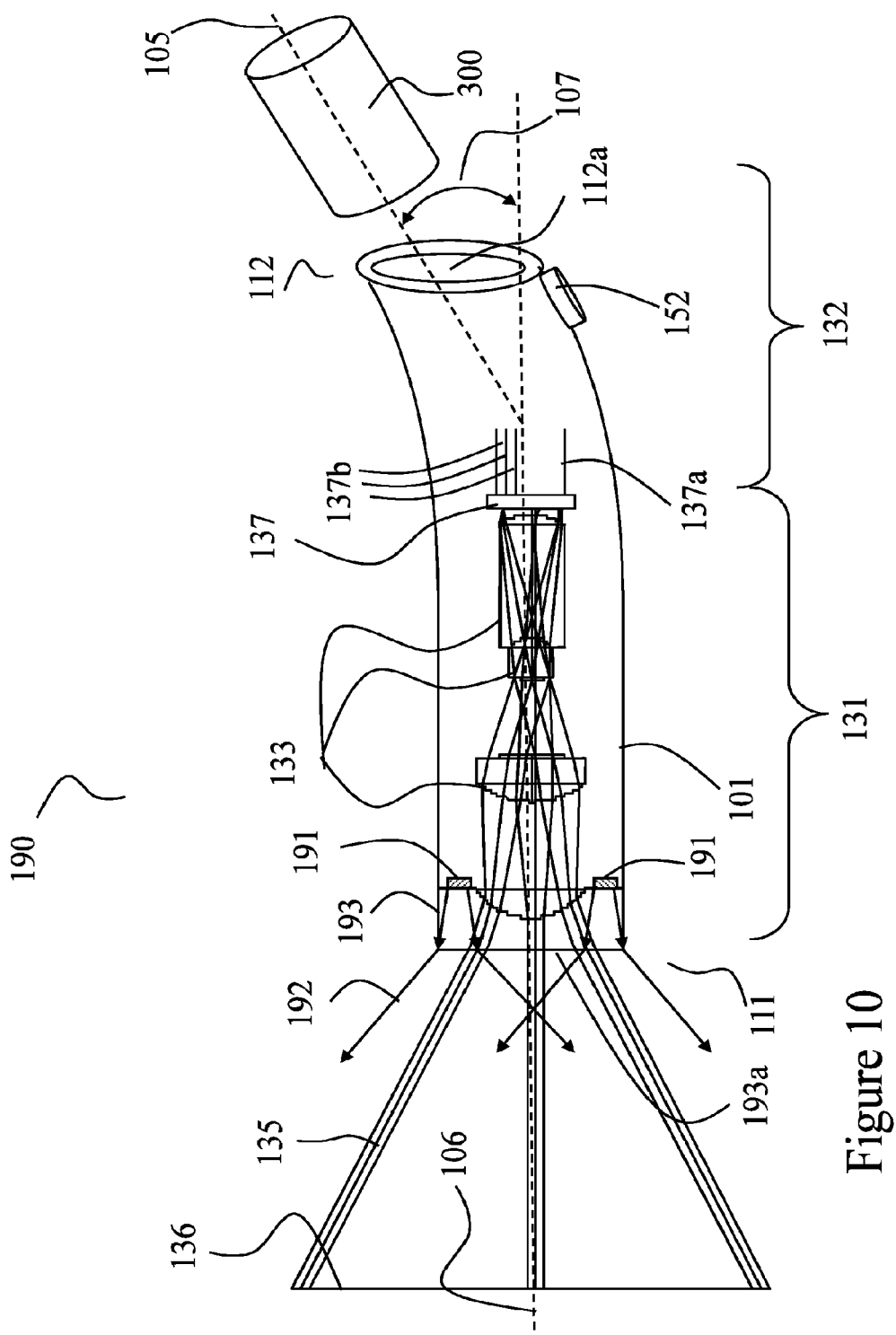
FIG. 10 illustrates fixed solid state illuminators assembled behind the first negative lens of the endoscope, used as window at the distal end of a flexible endoscope.

In an embodiment of a solid state illumination within a flexible endoscope 190, FIG. 10 illustrates the incorporation of white, color LEDs or lasers, IR or UV solid state light sources (chips) 191 behind the first negative lens 193 of the objective lens 133. This portion of the objective lens 193 in effect acts as a window (193a) for the illumination sources 191 (as well as imaging rays 135 as depicted in FIGS. 10, 11a-b, 13a-b, 14a-b, 15a-b and 16a-b), since the concave portion of the first negative lens of the objective, is typically much smaller than the distal window of the scope. Solid state illumination sources in this configuration can be directly mounted to this glass window around the concave area of the lens. As the illumination light leaves the glass at the distal end, the angular radiation pattern 192 of the light expands as illumination is emitted outside the glass. Refractive, polarization, or wave-plates can also be implemented in the area of the negative lens 193 beyond the concave portion (193a) to modify the illumination characteristic.

Figure 11A:
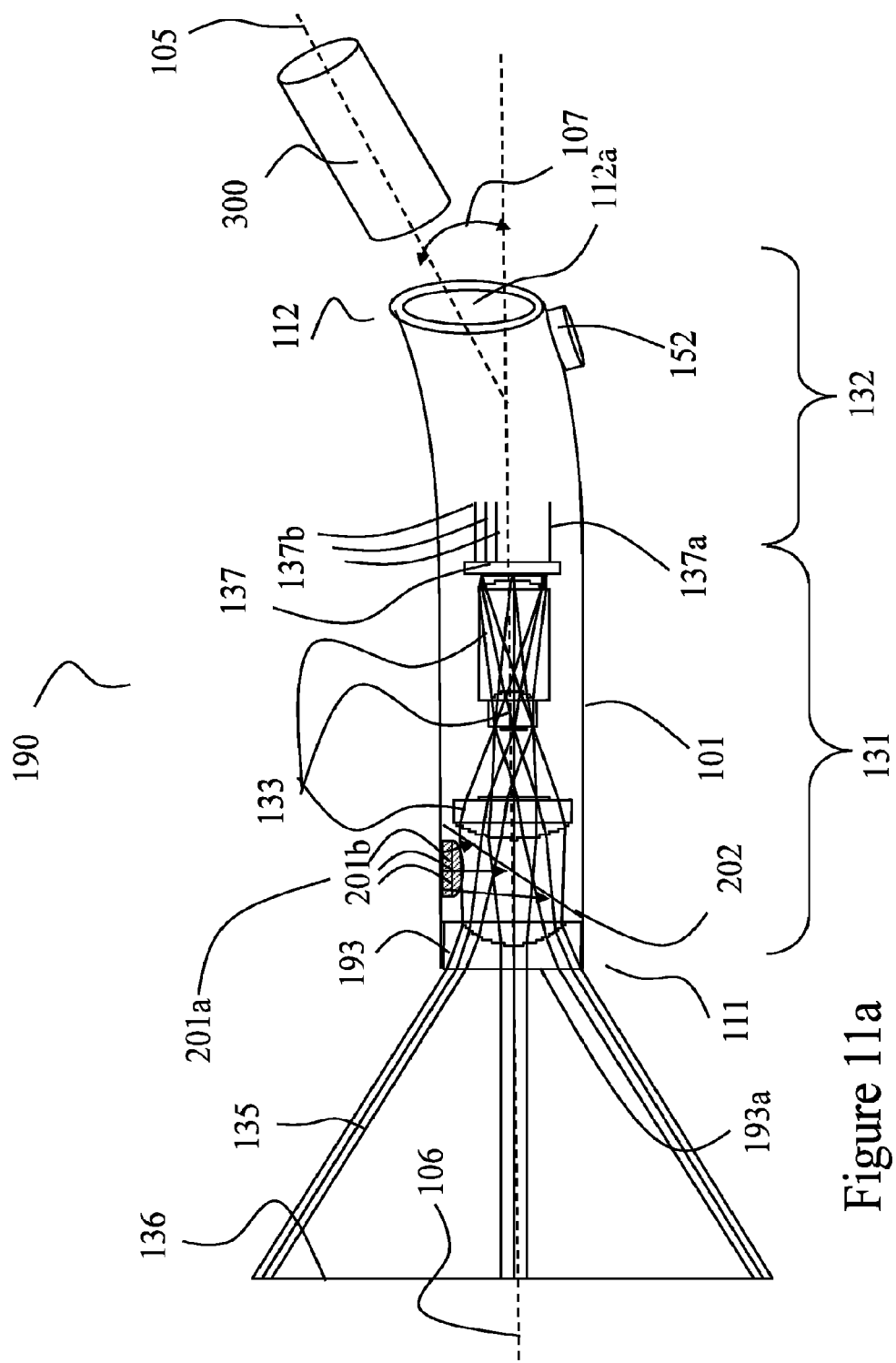
FIGS. 11a and 11b illustrate inclusion of the LED sources within the objective lens of an endoscope, using a beam splitter.

In yet another embodiment of LED illumination (201a) within the endoscope 190, white or combination of RGB LED chips, 201b can be used within the objective lens 133. As illustrated in FIG. 11a, LEDs 201b can be mounted so that the illumination 192 crosses the endoscope imaging axis 106 (center of imaging rays 135), where the illumination light from the LEDs 201b is combined into the imaging path (axis 106) using beam splitter optics 202.

Figure 11B:
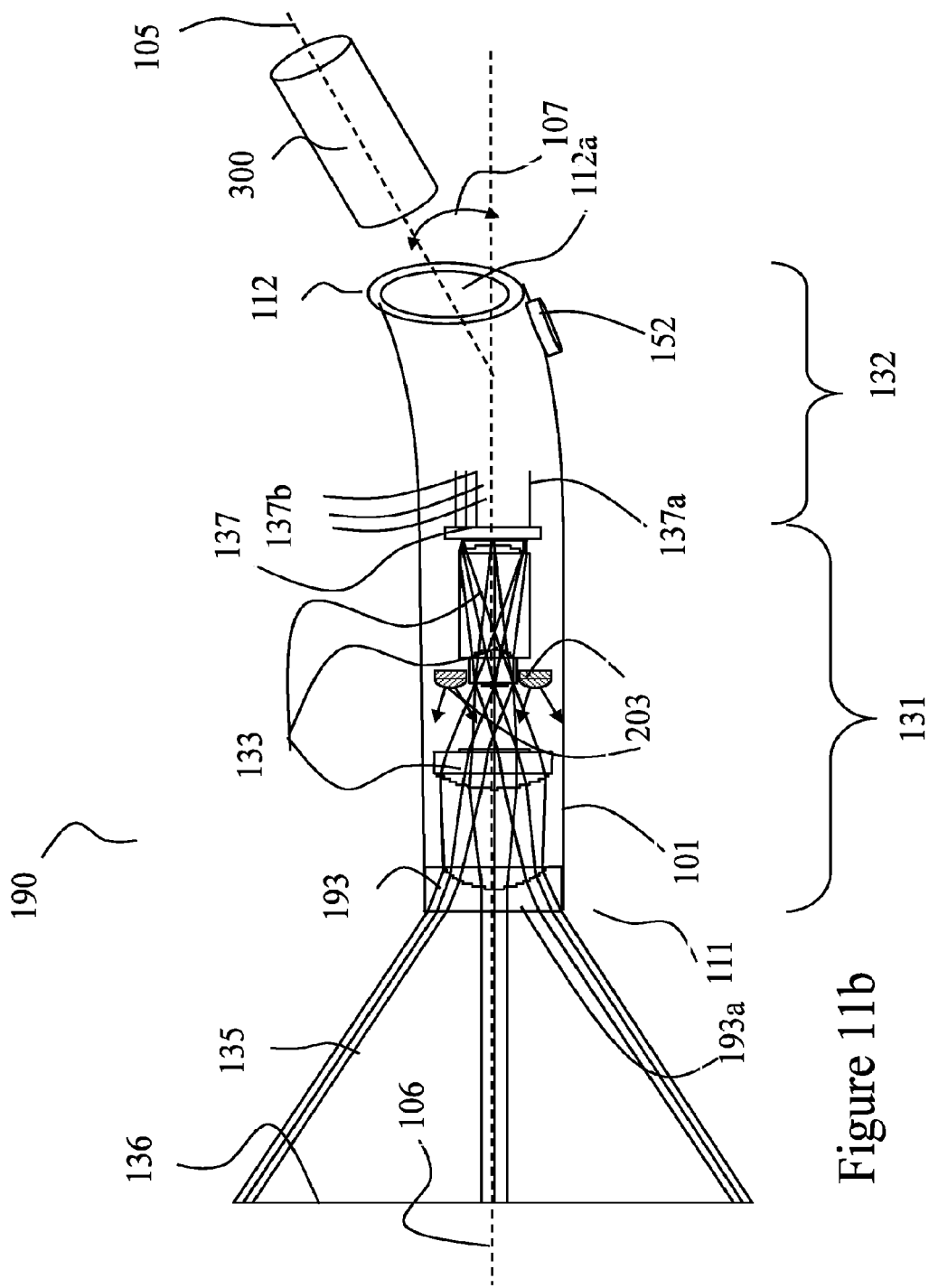

FIG. 11b illustrates an alternative positioning of the LEDs 203 within the objective lens 133 in LED illuminated endoscope 190, without the use of a beam splitter. Light emitted by the LEDs 203 in this geometry pass through the distal portion 111 of the objective lens 133, illuminating the surgical site 136 through the same window (193a) as the endoscope imaging optics 133 (imaging rays 135).

LEDs provide a desirable cost advantage over conventional lamp and fiber guide systems, as it replaces the expensive light sources, long fiber optic light guides to transfer light from the light source to the scope port 102, and the illumination light guides (123 and 138 in FIGS. 3 and 4) inside the scope body 101 as well. Low level power is only needed for the LED light sources, thus the electrical connection of the LEDs 152 is much easier (over the hollow tubular body 101 as seen in FIGS. 6a-b, 7, 9a, 10, 11a-b, 13a-b, 14a-b, 15a-b and 16a-b, 17a-c).

In each of the embodiments depicted in FIGS. 9a-b, 10, 11a-b, 13a-b, 14a-b, 16a-b only electrical power 152 and LED control signals need to be provided for the endoscope, eliminating the heavy and bulky fiber optics illumination cable connection (102) to the scope (130 and 140 in FIGS. 3 and 4), increasing the maneuverability of the endoscope. LED illumination systems are also more robust to shock and vibrations or extreme environmental conditions than the fiber optic illumination systems (123 in FIG. 3, and 138 in Figure).

Since any heat generated from the LEDs is not in the form of radiative heat, as in the case of lamps, it can be easily conducted out of the endoscope, or instrument tip (111 in FIGS. 7, 8, 9a-b, 10, 11a-b, 13a-b, 14a-b, 15a-b, 16a-b, 17a-c) using a conductive layer or the endoscope or instrument body (101) itself. Some of this heat can in fact be conducted towards the endoscope optical window 193a, such as in the embodiment of FIG. 10 which shows endoscope 190, where the LEDs 191 are at intimate contact with the endoscope window 193a and its holder (in FIGS. 13a-b), which provides the proper temperature setting to avoid any condensation on the optical window 193a, during operation and additionally warms the distal end 111 of the cold endoscope 190 when it is inserted into the warm and humid body cavity. In turn a separate low power infrared LED can also be used for the purpose of heating the endoscope tip.

In addition to the above exemplary embodiments 180 and 190 (FIGS. 9, 10, 11a-b), where the LED illuminators are used in fixed positions within the endoscope body 101, other deployable embodiments (FIGS. 12, 13a-b, 14a-b, 15a-b, 16a-b, and 17a-b), are possible for effective illumination of the surgical site 136. In these deployable embodiments, the LED illuminators (205a, 210a, 220a, 230a, 240a, 250a, all mounted at the distal end 111 of the hollow tubular body 101) are deployable from an insertion position in which they are held within the insertion body (101) or within a close profile of the insertion body (101), to an operational position where they are conveniently pointed to the object of interest. In operational position, the illumination light 192 can be directed to the surgical site 136 from beyond the endoscope body 101, where deployment of the LED holder structure positions the illuminators off axis from the imaging axis 103 (center of imaging rays 135), increasing the collection efficiency of the imaging optics.

In some exemplary embodiments, this deployment can be accomplished using, by way of example and not limitation, an umbrella type deployment structure capable of being opened and closed by an operator. Different variations of this umbrella structure can be used depending on the desired application, amount of illumination, and light positioning requirement. FIG. 12a illustrates one example of an umbrella-type deployment structure where an LED-supporting structure 205a is deployed through cannula 200 (with cannula body 101, distal opening 111a, and proximal opening 112a). A circular flexible membrane 205a is populated with white or color LED chips 205. This populated membrane 205a includes a spring at its peripheral section (circular edge 205b) of the membrane body 205a. The membrane 205a is deployably coupled to the distal end 111 of the cannula 200. In the insertion position, the membrane 205a is collapsed into a tube form (inside body 101 in FIG. 12a). Once the collapsed membrane 205a FIG. 12a, is maneuvered to the desired location, the membrane is fully deployed until it is outside the distal end 111 (opening 111a) of the cannula 200. The spring action at the membrane's edge 205b forces the membrane to open into a flat surface 205a in FIG. 12b. LEDs 205 illuminate the surgical site where other tools and instruments 300 can be inserted into the body through hollow tubular body 101.

Figure 13A:
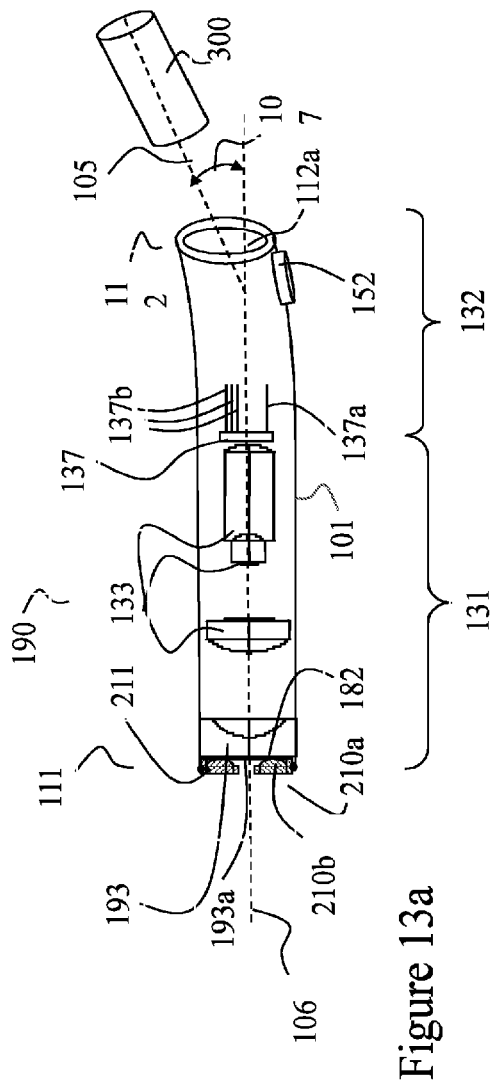
FIGS. 13a and 13b illustrate possible deployment of LED illuminators at the distal end of a flexible endoscope.
Figure 13B:
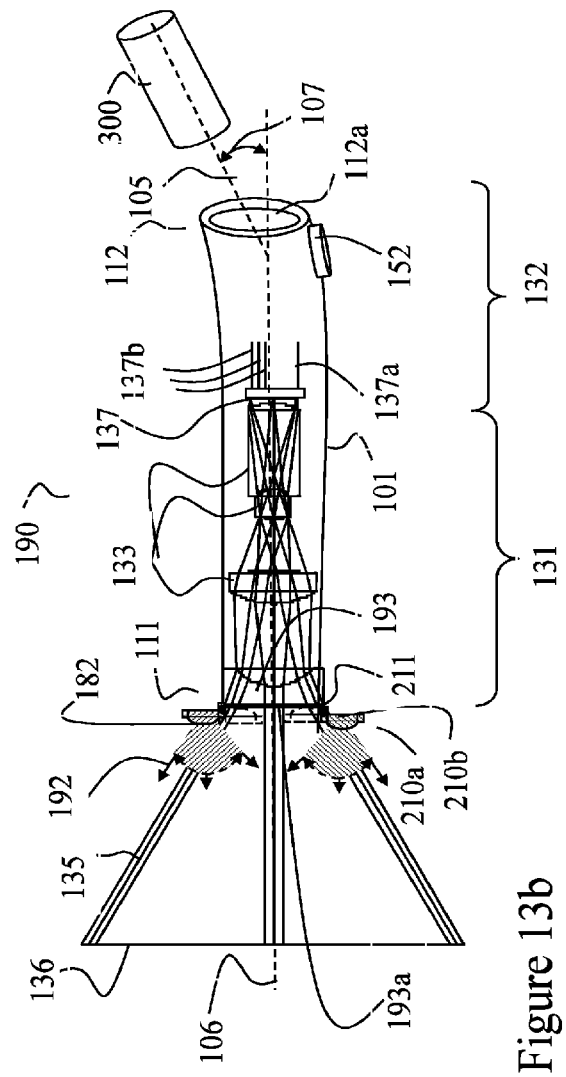

FIGS. 13a and 13b illustrate another embodiment of dynamic deployment of LED illuminators 210a. In FIG. 13a LED illuminators 210a are shown in their "LED off" or insertion position. In order to deploy LEDs 210b (encapsulated by lens 182), the illuminators 210a are flipped over the endoscope tip (around hinges 211). Once the illuminators 210a are deployed ("LED on" position), the 210b LEDs are flipped into position around the endoscope 190, distal tip 111, as shown in FIG. 13b.

Figure 14A:
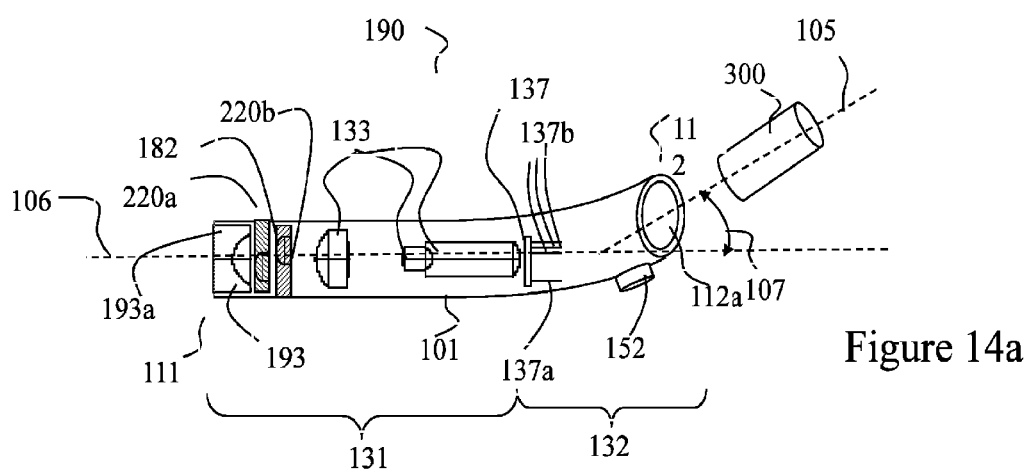
FIGS. 14a and 14b illustrate possible deployment of LED illuminators stored within the objective lens of a flexible endoscope.
Figure 14B:
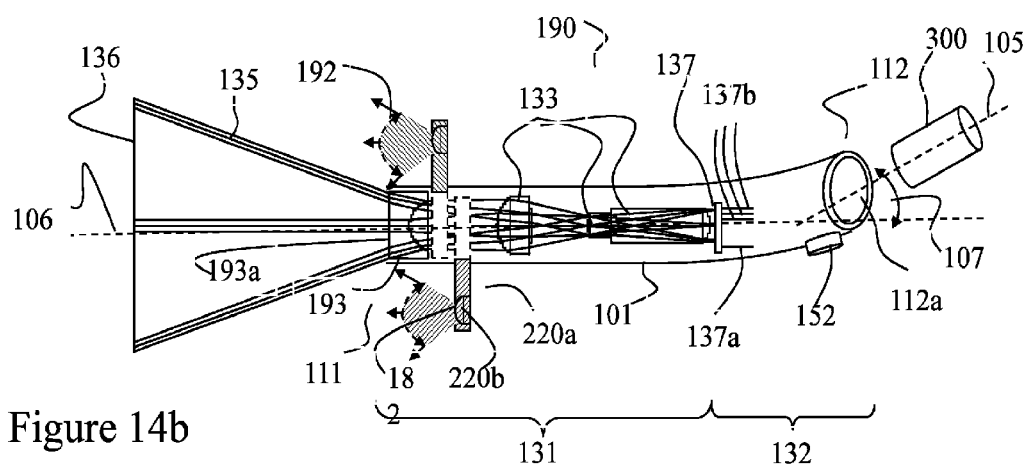

In another embodiment of deployable LED illumination, FIG. 14a represents an "LED off" position for the LED illuminators 220a as they are stored within the endoscope objective lens free cavity. In an "LED on" position, LED chips 220b are deployed in a circular manner, rotating outside the objective lens 133 cavity of the endoscope 190.

FIGS. 15a and 15b, represent anther scheme in storing 230a LED illuminators in their "LED off" position, next to the objective lens 122 at the distal end 111 of the endoscope body 101, in FIG. 15a. LEDs illuminators 230a are disposed on a hinge portion 232. The hinge portion 232 is, in turn, connected to an actuation portion 233. The LED illuminators 230a are deployed into position as the actuation portion 233 is pushed distally in the direction of the arrows towards the distal tip 111 of the endoscope. Such action deploys the hinge portion 232 which positions the LED chips 230b to emit light that is off-axis from the imaging optics axis 106, FIG. 15b.

In an alternate configuration, represented in FIGS. 16a and 16b, another type of deployment mechanism is used. The LEDs illuminators 240a are disposed on hinge portion 242. The hinge portion 242 is, in turn, connected to an actuation portion 243. The LED illuminators 240a are deployed into positions by pulling the actuation portion 243 proximally in the direction of the arrows toward the proximal end 112 of the endoscope 180, deploying the LED chips 240b into their "LED on" position.

FIGS. 17a through 17c illustrate an exemplary embodiment of LED illumination tubular body 101, in conjunction with a surgical tool 300b. FIGS. 17a and 17b are side views of the surgical tool in an illumination "off" position. FIG. 17c illustrates surgical tool 300b in an illumination 250b or deployed "LED on" position, where LEDs illuminators 250 are opened up from the stored position to illuminate the surgical work area.

In alternate embodiments of all of the endoscopes, cannulas and other devices (body 101) described above (FIGS. 6a through 17c) that use LEDs for illumination, Solid State Laser Diodes (LD) can also be used at the distal end of tools, insertion tubes, catheters, imaging scopes, cannulas, etc. Infrared Imaging could use IR solid state light sources to illuminate intra-vein or close tissue diagnostic and surgical procedures. IR detectors and cameras are used for thorough tissue and blood imaging along with external infrared light sources that have appreciable penetration depth in human tissue, blood or other bodily fluids such as urine. Using a high intensity IR source at the surgical or examination site with control over the intensity, radiation pattern, and the direction of illumination helps with the most critical surgical procedures inside the vein, heart and other body organs.

Scanning or other directing mechanical elements 300 could also be used (inserted through the proximal opening 112a) to adjust the direction of illumination and control of the solid state light sources (laser diodes, and LEDs) used in conjunction with variety of surgical instruments inside the body (FIGS. 11a-b, 13a-b, 14a-b), where other scanning or non-scanning image capture elements detect the light. Additionally, since power (from 152) is provided to the solid state light source at the distal end 111 of the probe or scope 101, resistive heat from part of the electrical signal can also be used to reduce condensation at the probe or scope window 193a in FIGS. 9, 10, 11a-b, 13a-b, 14a-b, 15a-b and 16a-b.

By placing the illumination light sources at close proximity of the object inside the body (distal end 111) in diagnostic or surgical procedures (FIGS. 6a through 17c), the losses in conjunction with the transmission of light from the external source to the surgical site is eliminated. Thus, light sources that have equal efficiency in converting electrical power to useful light, can be operated in much lower input power, eliminating the need for sophisticated power and heat management. Power and control signals (from electrical connection 152) transmitting through appropriate wires and flex circuitry (152a, 137a, 137b), can be easily routed along the tool or endoscope body 101 to the light source (LED chips 151, 161, 171, 181b, 191, 201b, 203, 205, 210b, 220b, 230b, 240b, 250a in (FIGS. 6a through 17c).

Miniature, optical components such as lenses (182), mirrors (162), beam splitters (202), polarizers, waveplates, etc. can also be used in conjunction with solid state light sources (laser diodes and LEDs), to further manipulate the illumination characteristics of the light. Lenses (182) for example, can be used to direct the light to larger or smaller areas of the scene 124 and 136, or focusing the beam to a small area on the object depending on the application.

Polarization characteristics of the solid state laser or polarized LED light output can also be used in special detection schemes, where depth perception or other biological imaging characteristics that depend on the polarization of the light can be better perceived, similar to polarized microscopy.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for illuminating a body cavity, comprising:
   a bendable elongate tube devoid of fiber light guides, the elongate tube including an internal lumen with an interior diameter extending between a distal opening at a distal end and a proximal opening at a proximal end opposite the distal end;
   at least one optically transmissive lens element occluding the entire interior diameter of the internal lumen of the elongate tube;
   an image sensor fixed to the elongate tube at a distal portion of the elongate tube proximate the distal end; and
   at least one deployable element including a solid-state light source, the at least one deployable element rotatably coupled to the distal portion and configured to rotate about an axis transverse to a longitudinal axis of the distal end between an insertion position relative to the elongate tube and a deployed position relative to the elongate tube, such that in the insertion position the solid-state light source is disposed distally relative to the distal end of the elongated tube, and wherein the at least one deployable element is positioned within the profile of the elongate tube in the insertion position, and is positioned outside the profile of the elongate tube in the deployed position.

2. The device of claim 1, further comprising at least one optical element disposed in the elongate tube, wherein the solid-state light source is configured to provide illumination at at least one electromagnetic wavelength and to be selectively turned on or off.

3. The device of claim 2, wherein the image sensor is a CCD or CMOS camera chip and is configured to receive images from the at least one optical element disposed in the elongate tube.

4. The device of claim 3, wherein a specified electromagnetic wavelength generated by the solid-state light source is time synchronized with the CCD or CMOS camera chip to enable detection of images from the specified electromagnetic wavelength at specified time intervals.

5. The device of claim 3, wherein the CCD or CMOS camera chip is a black and white imaging sensor that is time synchronized with color illumination provided by LED chips of the solid-state light source, the LED chips configured to generate a plurality of electromagnetic wavelengths.

6. The device of claim 1, wherein the at least one lens element covers the distal end of the elongate tube.

7. The device of claim 1, further comprising electrical lines imbedded in the elongate tube to provide power to the solid-state light source.

8. The device of claim 1, wherein the at least one deployable element is positioned proximate the elongate tube in the insertion position and is positioned a distance from the elongate tube in the deployed position.

9. The device of claim 1, wherein the at least one deployable element is positioned within the profile of the elongate tube and distally of the at least one lens element in the insertion position, and is positioned outside the profile of the elongate tube in the deployed position.

10. A device for insertion into a body cavity, comprising:
    a bendable elongate tube with an internal lumen with an interior diameter extending between a distal opening at a distal end and a proximal opening at a proximal end opposite the distal end;
    at least one window covering the entire interior diameter of the internal lumen at the distal end of the elongate tube; and
    at least one deployable element including at least one light source, the at least one deployable member rotatably coupled to the elongate tube at or near the distal end and configured to rotate about an axis transverse to a longitudinal axis of the distal end between an insertion position and a deployed position, such that in the insertion position the solid-state light source is disposed distally relative to the distal end of the elongated tube, and wherein the at least one deployable element is positioned within the profile of the elongate tube in the insertion position, and is positioned outside the profile of the elongate tube in the deployed position.

11. The device of claim 10, wherein the at least one window comprises at least one lens.

12. The device of claim 10, wherein the at least one deployable member is rotatably coupled to the distal portion of the elongate tube via a rotational hinge, the rotational hinge rotating about the axis transverse to the longitudinal axis of the distal end.

13. The device of claim 12, wherein the axis transverse to the longitudinal axis of the distal end is orthogonal relative to the longitudinal axis of the distal end.

* * * * *